United States Patent [19]
Müller et al.

[11] Patent Number: 5,151,514
[45] Date of Patent: Sep. 29, 1992

[54] HERBICIDAL SUBSTITUTED 4-SULPHONYLAMINO-2-AZINYL-1,2,4-TRIAZOL-3-ONES

[75] Inventors: Klaus-Helmut Müller, Duesseldorf; Rolf Kirsten, Monheim; Joachim Kluth, Langenfeld; Klaus König, Odenthal; Hans-Jochem Riebel; Peter Babczinski, both of Wuppertal; Hans-Joachim Santel, Leverkusen; Robert R. Schmidt, Bergisch Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 783,586

[22] Filed: Oct. 28, 1991

Related U.S. Application Data

[62] Division of Ser. No. 583,915, Sep. 17, 1990, Pat. No. 5,085,697, which is a division of Ser. No. 382,163, Jul. 19, 1989, Pat. No. 4,988,381.

[30] Foreign Application Priority Data

Jul. 28, 1988 [DE] Fed. Rep. of Germany ....... 3825602
Jan. 16, 1989 [DE] Fed. Rep. of Germany ....... 3901084

[51] Int. Cl.⁵ .......................................... C07D 403/04
[52] U.S. Cl. ................................. 544/212; 544/198; 544/207; 544/209
[58] Field of Search ............... 544/198, 209, 212, 207

[56] References Cited

U.S. PATENT DOCUMENTS 4,988,811  1/1991  Valbuss et al. .................... 544/198

Primary Examiner—Patricia L. Morris
Attorney, Agent, or Firm—Sprung Horn Kramer & Woods

[57] ABSTRACT

Herbicidal substituted sulphonylaminotriazolinones of the formula in which
$R^1$ represents an optionally substituted radical from the group consisting of alkyl, aralkyl, aryl and heteroaryl,
$R^2$ represents hydrogen or the group $-SO_2-R^1$ where $R^1$ has the abovementioned meaning,
$R^3$ represents hydrogen, halogen, hydroxyl, mercapto, amino or an optionally substituted radical from the group consisting of alkyl, cycloalkyl, aralkyl, aryl, alkoxy, alkenyloxy, alkinyloxy, alkylthio, alkylsulphinyl, alkylsulphonyl, alkenylthio, alkinylthio, aralkoxy, aralkylthio, alkylamino and dialkylamino,
$R^4$ represents hydrogen, halogen, hydroxyl, amino or an optionally substituted radical from the group consisting of alkyl, alkoxy, alkylthio, alkylsulphinyl, alkylsulphonyl, alkylamino and dialkylamino,
X represents nitrogen or a CH group,
Y represents nitrogen or a $CR^5$ group where
$R^5$ represents hydrogen, halogen, cyano, alkyl, formyl, alkylcarbonyl or alkoxycarbonyl, and
Z represents nitrogen or a $CR^6$ group where
$R^6$ represents hydrogen, halogen, hydroxyl, amino or an optionally substituted radical from the group consisting of alkyl, alkoxy, alkylthio, alkylsulphinyl, alkylsulphonyl, alkylamino and dialkylamino, and salts thereof. Intermediates of the formulas and are also new.

6 Claims, No Drawings

HERBICIDAL SUBSTITUTED 4-SULPHONYLAMINO-2-AZINYL-1,2,4-TRIAZOL-3-ONES

This is a division of application Ser. No. 583,915, filed Sep. 17, 1990, now U.S. Pat. No. 5,085,687, which is a division of application Ser. No. 382,163, filed Jul. 19, 1989, now U.S. Pat. No. 4,988,381.

The new substituted sulphonylaminotriazolinones of the general formula (I) are obtained when (a) substituted aminotriazolinones of the general formula (II)

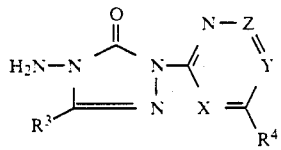
(II)

in which
$R^3$, $R^4$, X, Y and Z have the abovementioned meanings,
are reacted with sulphonyl halides or sulphonic anhydrides of the general formula (III)

$$R^1-SO_2-Q \quad (III)$$

in which
$R^1$ has the abovementioned meaning and
Q represents fluorine, chlorine, bromine or the group $-O-SO_2-R^1$, where
$R^1$ has the abovementioned meaning,
if appropriate, in the presence of an acid acceptor and, if appropriate, in the presence of a diluent, the resulting compounds of the formula (I) in which
$R^2$ represents the group $-SO_2-R^1$,
$R^3$ represents hydrogen, halogen, hydroxyl, mercapto, amino or an optionally substituted radical from the series comprising alkyl, cycloalkyl, aralkyl, aryl, alkoxy, alkenyloxy, alkinyloxy, alkylthio, alkylsulphinyl, alkylsulphonyl, alkenylthio, alkinylthio, aralkoxy, aralkylthio, alkylamino and dialkylamino,
$R^4$ represents hydrogen, halogen, hydroxyl, amino or an optionally substituted radical from the series comprising alkyl, alkoxy, alkylthio, alkylsulphinyl, alkylsulphonyl, alkylamino and dialkylamino,
X represents nitrogen or a CH group,
Y represents nitrogen or a $CR^5$ group where
$R^5$ represents hydrogen, halogen, cyano, alkyl, formyl, alkylcarbonyl or alkoxycarbonyl, and
Z represents nitrogen or a $CR^6$ group where
$R^6$ represents hydrogen, halogen, hydroxyl, amino or an optionally substituted radical from the series comprising alkyl, alkoxy, alkylthio, alkylsulphinyl, alkylsulphonyl, alkylamino and dialkylamino,
and salts of compounds of the formula (I) have now been found.
are reacted, if appropriate, with desulphonylating agents, if appropriate in the presence of diluents, to give compounds of the formula (I) in which
$R^2$ represents hydrogen,
and, if appropriate, salts are prepared therefrom by customary methods or when
b) sulphonylaminotriazolinones of the general formula (IV)

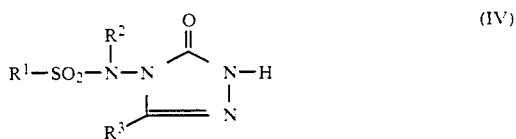
(IV)

in which
$R^1$, $R^2$ and $R^3$ have the above-mentioned meanings, are reacted with azines of the general formula (V)

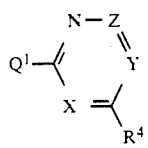
(V)

in which
$R^4$, X, Y and Z have the above-mentioned meanings and
$Q^1$ represents halogen, benzylsulphonyl or alkylsulphonyl,
if appropriate, in the presence of an acid acceptor and, if appropriate, in the presence of a diluent and, if appropriate, salts are prepared by customary methods from the resultant compounds of the formula (I).

The new substituted sulphonylaminotriazolinones of the general formula (I) are distinguished by powerful herbicidal activity. These compounds represent a chemically novel class of herbicides. Surprisingly, the new compounds of the formula (I) show a considerably better herbicidal action than 4-(3-trifluoromethoxy-benzylideneamino)-2,4-dihydro-3H-1,2,4-triazol-3-one, which is known and has similar structure.

The invention preferably relates to compounds of the formula (I) in which
$R^1$ represents the radical

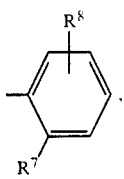

where
$R^7$ and $R^8$ are identical or different and represent hydrogen, fluorine, chlorine, bromine, iodine, cyano, nitro, $C_1$-$C_6$-alkyl [which is optionally substituted by fluorine, chlorine, bromine, cyano, carboxyl, $C_1$-$C_4$-alkoxycarbonyl, $C_1$-$C_4$-alkylaminocarbonyl, di-($C_1$-$C_4$-alkyl)aminocarbonyl, hydroxyl, $C_1$-$C_4$-alkoxy, formyloxy, $C_1$-$C_4$-alkyl-carbonyloxy, $C_1$-$C_4$-alkoxy-carbonyloxy, $C_1$-$C_4$-alkylamino-carbonyloxy, $C_1$-$C_4$-alkylthio, $C_1$-$C_4$-alkylsulphinyl, $C_1$-$C_4$-alkylsulphonyl, di-($C_1$-$C_4$-alkyl)-aminosulphonyl, $C_3$-$C_6$-cycloalkyl or phenyl], represent $C_2$-$C_6$-alkenyl [which is optionally substituted by fluorine, chlorine, bromine, cyano, $C_1$-$C_4$-alkoxy-carbonyl, carboxyl or phenyl], represent $C_2$-$C_6$-alkinyl [which is optionally substituted by fluorine, chlorine, bromine, cyano, $C_1$-$C_4$-alkoxy-carbonyl, carboxyl or phenyl], represent $C_1$-$C_4$-alkoxy [which is optionally substituted by fluorine, chlorine, bromine, cyano, carboxyl, $C_1-C_4$-alkoxy-carbonyl, $C_1-C_4$-alkoxy, $C_1-C_4$-alkylthio, $C_1-C_4$-alkylsulphinyl or $C_1-C_4$-alkylsulphonyl], represent $C_1-C_4$-alkylthio [which is optionally substituted by fluorine, chlorine, bromine, cyano, carboxyl, $C_1-C_4$-alkoxy-carbonyl, $C_1-C_4$-alkylthio, $C_1-C_4$-alkylsulphinyl or $C_1-C_4$-alkylsulphonyl], represent $C_3-C_6$-alkenyloxy [which is optionally substituted by fluorine, chlorine, bromine, cyano or $C_1-C_4$-cyano or $C_1-C_4$-alkoxy-carbonyl], represent $C_2-C_6$-alkenylthio [which is optionally substituted by fluorine, chlorine, bromine, cyano, nitro, $C_1-C_3$-alkylthio or $C_1-C_4$-alkoxycarbonyl], $C_3-C_6$-alkinyloxy, $C_3-C_6$-alkinylthio or represent the radical $-S(O)_p-R^9$, where p represents the numbers 1 or 2 and $R^9$ represents fluorine, $C_1-C_4$-alkyl [which is optionally substituted by fluorine, chlorine, bromine, cyano or $C_1-C_4$-alkoxy-carbonyl], $C_3-C_6$-alkenyl, $C_3-C_6$-alkinyl, $C_1-C_4$-alkoxy, $C_1-C_4$-alkoxy-$C_1-C_4$-alkylamino, $C_1-C_4$-alkylamino, di-($C_1-C_4$-alkyl)-amino or represents the radical $-NHOR^{10}$, where $R^{10}$ represents $C_1-C_6$-alkyl [which is optionally substituted by fluorine, chlorine, cyano, $C_1-C_4$-alkoxy, $C_1-C_4$-alkylthio, $C_1-C_4$-alkylsulphinyl, $C_1-C_4$-alkylsulphonyl, $C_1-C_4$-alkylcarbonyl, $C_1-C_4$-alkoxy-carbonyl, $C_1-C_4$-alkylaminocarbonyl or di-($C_1-C_4$-alkyl)-amino-carbonyl], represents $C_3-C_6$-alkenyl [which is optionally substituted by fluorine, chlorine or bromine], $C_3-C_6$-alkinyl, $C_3-C_6$-cycloalkyl, $C_3-C_6$-cycloalkyl-$C_1-C_2$-alkyl, phenyl-$C_1-C_2$-alkyl [which is optionally substituted by fluorine, chlorine, nitro, cyano, $C_1-C_4$-alkyl, $C_1-C_4$-alkoxy or $C_1-C_4$-alkoxycarbonyl], represents benzhydryl or represents phenyl [which is optionally substituted by fluorine, chlorine, nitro, cyano, $C_1-C_4$-alkyl, trifluoromethyl, $C_1-C_4$-alkoxy, $C_1-C_2$-fluoroalkoxy, $C_1-C_4$-alkylthio, trifluoromethylthio or $C_1-C_4$-alkoxycarbonyl], $R^7$ and/or $R^8$ furthermore represent phenyl or phenoxy, $C_1-C_4$-alkylcarbonylamino, $C_1-C_4$-alkoxycarbonylamino, $C_1-C_4$-alkylaminocarbonyl-amino, di-($C_1-C_4$-alkyl)-aminocarbonylamino, or represent the radical $-CO-R^{11}$, where $R^{11}$ represents $C_1-C_6$-alkyl, $C_1-C_6$-alkoxy, $C_3-C_6$-cycloalkoxy, $C_3-C_6$-alkenyloxy, $C_1-C_4$ alkylthio, $C_1-C_4$-alkylamino, $C_1-C_4$-alkoxyamino, $C_1-C_4$-alkoxy-$C_1-C_4$-alkyl-amino or di-($C_1-C_4$-alkyl)-amino [which are optionally substituted by fluorine and/or chlorine], $R^7$ and/or $R^8$ furthermore represent $C_1-C_4$-alkyl-sulphonyloxy, di-($C_1-C_4$-alkyl)-aminosulphonylamino or the radical $-CH=N-R^{12}$, where $R^{12}$ represents $C_1-C_6$-alkyl which is optionally substituted by fluorine, chlorine, cyano, carboxyl, $C_1-C_4$-alkoxy, $C_1-C_4$-alkylthio, $C_1-C_4$-alkylsulphinyl or $C_1-C_4$-alkylsulphonyl, represents benzyl which is optionally substituted by fluorine or chlorine, represents $C_3-C_6$-alkenyl or $C_3-C_6$-alkinyl, each of which is optionally substituted by fluorine or chlorine, represents phenyl which is optionally substituted by fluorine, chlorine, bromine, $C_1-C_4$-alkyl, $C_1-C_4$-alkoxy, trifluoromethyl, trifluoromethoxy or trifluoromethylthio, represents $C_1-C_6$-alkoxy, $C_3-C_6$-alkenoxy, $C_3-C_6$-alkinoxy or benzyloxy, each of which is optionally substituted by fluorine and/or chlorine, represents amino, $C_1-C_4$-alkylamino, di-($C_1-C_4$-alkyl)-amino, phenylamino, $C_1-C_4$-alkyl-carbonylamino, $C_1-C_4$-alkoxy-carbonylamino, $C_1-C_4$-alkylsulphonylamino or represents phenylsulphonylamino which is optionally substituted by fluorine, chlorine, bromine or methyl, where furthermore $R^1$ represents the radical

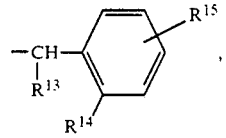

where $R^{13}$ represents hydrogen or $C_1-C_4$-alkyl, $R^{14}$ and $R^{15}$ are identical or different and represent hydrogen, fluorine, chlorine, bromine, nitro, cyano, $C_1-C_4$-alkyl [which is optionally substituted by fluorine and/or chlorine], $C_1-C_4$-alkoxy [which is optionally substituted by fluorine and/or chlorine], carboxyl, $C_1-C_4$-alkoxycarbonyl, $C_1-C_4$-alkylsulphonyl or di-($C_1-C_4$-alkyl)-aminosulphonyl; where furthermore $R^1$ represents the radical

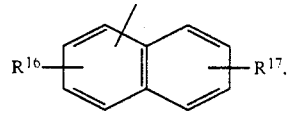

where $R^{16}$ and $R^{17}$ are identical or different and represent hydrogen, fluorine, chlorine, bromine, nitro, cyano, $C_1-C_4$-alkyl [which is optionally substituted by fluorine and/or chlorine] or $C_1-C_4$-alkoxy [which is optionally substituted by fluorine and/or chlorine]; where furthermore $R^1$ represents the radical

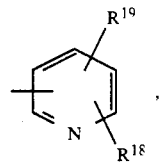

where $R^{18}$ and $R^{19}$ are identical or different and represent hydrogen, fluorine, chlorine, bromine, nitro, cyano, $C_1-C_4$-alkyl [which is optionally substituted by fluorine and/or chlorine], $C_2-C_4$-alkenyl [which is optionally substituted by fluorine and/or chlorine], $C_1-C_4$-alkoxy [which is optionally substituted by fluorine and/or chlorine], represents $C_1-C_4$-alkythio, $C_1-C_4$-alkylsulphinyl or $C_1-C_4$-alkylsulphonyl [which are optionally substituted by fluorine and/or chlorine], and represents di-($C_1-C_4$-alkyl)-aminosulphonyl, $C_1-C_4$-alkoxy-carbonyl, dimethylaminocarbonyl or dioxolanyl; where furthermore R¹ represents the radical

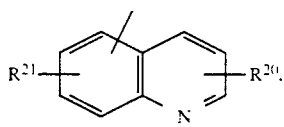

where
R²⁰ and R²¹ are identical or different and represent hydrogen, fluorine, chlorine, bromine, $C_1$-$C_4$-alkyl [which is optionally substituted by fluorine and/or bromine], $C_1$-$C_4$-alkoxy [which is optionally substituted by fluorine and/or chlorine], represent $C_1$-$C_4$-alkylthio, $C_1$-$C_4$-alkylsulphinyl or $C_1$-$C_4$-alkylsulphonyl [which are optionally substituted by fluorine and/or chlorine], or represent di-($C_1$-$C_4$-alkyl)-aminosulphonyl; where furthermore
R¹ represents the radical

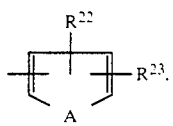

where
R²² and R²³ are identical or different and represent hydrogen, fluorine, chlorine, bromine, cyano, nitro, $C_1$-$C_4$-alkyl [which is optionally substituted by fluorine, chlorine, $C_1$-$C_4$-alkoxy and/or $C_1$-$C_4$-halogenoalkoxy], $C_1$-$C_4$-alkoxy [which is optionally substituted by fluorine and/or chlorine], $C_1$-$C_4$-alkylthio, $C_1$-$C_4$-alkylsulphinyl or $C_1$-$C_4$-alkylsulphonyl [which is optionally substituted by fluorine and/or chlorine], di-($C_1$-$C_4$-alkyl)-aminosulphonyl or $C_1$-$C_4$-alkoxycarbonyl, and
A represents oxygen, sulphur or the group N—Z¹, where
Z¹ represents hydrogen, $C_1$-$C_4$-alkyl [which is optionally substituted by fluorine, chlorine, bromine or cyano], $C_3$-$C_6$-cycloalkyl, benzyl, phenyl [which is optionally substituted by fluorine, chlorine, bromine or nitro], $C_1$-$C_4$-alkylcarbonyl, $C_1$-$C_4$-alkoxy-carbonyl or di-($C_1$-$C_4$-alkyl)-aminocarbonyl; where furthermore
R¹ represents the radical

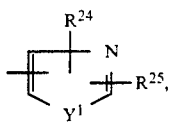

where
R²⁴ and R²⁵ are identical or different and represent hydrogen, $C_1$-$C_4$-alkyl, halogen, $C_1$-$C_4$-alkoxycarbonyl, $C_1$-$C_4$-alkoxy or $C_1$-$C_4$-halogenoalkoxy,
Y¹ represents sulphur or the group N—R²⁶, where
R²⁶ represents hydrogen or $C_1$-$C_4$-alkyl; where furthermore
R¹ represents the radical

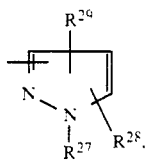

where
R²⁷ represents hydrogen, $C_1$-$C_4$-alkyl, benzyl, (iso)-quinolinyl or phenyl,
R²⁸ represents hydrogen, halogen, cyano, nitro, $C_1$-$C_4$-alkyl [which is optionally substituted by fluorine and/or chlorine], $C_1$-$C_4$-alkoxy [which is optionally substituted by fluorine and/or chlorine], dioxolanyl or $C_1$-$C_4$-alkoxy-carbonyl and
R²⁹ represents hydrogen, halogen or $C_1$-$C_4$-alkyl; where furthermore
R¹ represents the radical

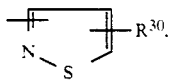

where
R³⁰ represents hydrogen, halogen, $C_1$-$C_4$-alkyl, $C_1$-$C_4$-halogenoalkyl, $C_1$-$C_4$-alkoxy, $C_1$-$C_4$-halogenoalkoxy or $C_1$-$C_4$-alkoxy-carbonyl; where furthermore
R¹ represents the radical

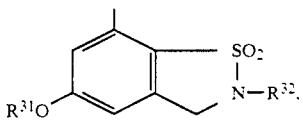

where
R³¹ represents $C_1$-$C_4$-alkyl and
R³² represents $C_1$-$C_4$-alkyl; where furthermore
R¹ represents the radical

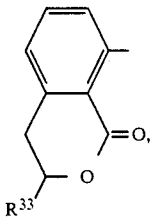

where
R³³ represents hydrogen or methyl, in which furthermore
R² represents hydrogen or the group —$SO_2$—R¹, where
R¹ has the meaning indicated above as preferred; in which furthermore
R³ represents hydrogen, fluorine, chlorine, bromine, iodine, hydroxyl, mercapto, amino or an optionally fluorine- and/or chlorine-substituted radical from the series comprising $C_1$-$C_4$-alkyl, $C_3$-$C_6$-cycloalkyl, benzyl, phenyl, $C_1$-$C_4$-alkoxy, $C_3$-$C_4$-alkenyloxy, $C_3$-$C_4$-alkinyloxy, $C_1$-$C_4$-alkylthio, $C_1$-$C_4$-alkylsulphinyl, $C_1$-$C_4$-alkylsulphonyl, $C_3$-$C_4$-alkenylthio, $C_3$-$C_4$-alkinylthio, benzyloxy, benzylthio, $C_1$-$C_4$-alkylamino and di-($C_1$-$C_4$-alkyl)-amino, $R^4$ represents hydrogen, fluorine, chlorine, bromine, hydroxyl, amino, $C_1$-$C_4$-alkyl, $C_1$-$C_4$-halogenoalkyl, $C_1$-$C_2$-alkoxy-$C_1$-$C_2$-alkyl, $C_1$-$C_4$-alkoxy, $C_1$-$C_4$-halogenoalkoxy, $C_1$-$C_2$-alkoxy, $C_1$-$C_4$-alkylthio, $C_1$-$C_4$-halogenoalkylthio, $C_1$-$C_4$-alkylsulphinyl, $C_1$-$C_4$-alkylsulphonyl, $C_1$-$C_4$-alkylsulphinyl, $C_1$-$C_4$-alkylamino or di-($C_1$-$C_2$-alkyl)-amino, X represents nitrogen or a CH group, Y represents nitrogen or a $CR^5$ group where
 $R^5$ represents hydrogen, fluorine, chlorine, bromine, cyano, methyl, formyl, acetyl, methoxycarbonyl or ethoxycarbonyl and Z represents nitrogen or a $CR^6$ group where
 $R^6$ represents hydrogen, fluorine, chlorine, bromine, $C_1$-$C_4$-alkyl, $C_1$-$C_4$-alkoxy, $C_1$-$C_4$-halogenoalkoxy, $C_1$-$C_4$-alkylthio, $C_1$-$C_4$-alkylsulphinyl, $C_1$-$C_4$-alkylsulphonyl, $C_1$-$C_4$-alkylamino, dimethylamino or diethylamino.

The invention particularly relates to compounds of the formula (I) in which
$R^1$ represents the radical

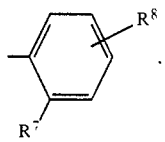

where
 $R^7$ represents fluorine, chlorine, bromine, methyl, trifluoromethyl, methoxy, difluoromethoxy, trifluoromethoxy, $C_1$-$C_3$-alkylthio, $C_1$-$C_3$-alkylsulphinyl, $C_1$-$C_3$-alkylsulphonyl, dimethylaminosulphonyl, N-methoxy-N-methylaminosulphonyl, phenyl, phenoxy or $C_1$-$C_3$-alkoxycarbonyl and
 $R^8$ represents hydrogen, fluorine or chlorine; where furthermore
$R^1$ represents the radical

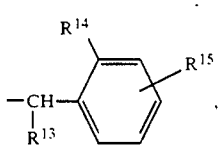

where
 $R^{13}$ represents hydrogen,
 $R^{14}$ represents fluorine, chlorine, bromine, methyl, methoxy, difluoromethoxy, trifluoromethoxy, ethoxy, methoxycarbonyl, ethoxycarbonyl, methylsulphonyl or dimethylaminosulphonyl and
 $R^{15}$ represents hydrogen; where furthermore
$R^1$ represents the radical

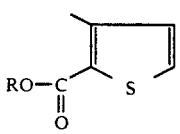

where
 R represents $C_1$-$C_4$-alkyl, or
$R^1$ represents the radical

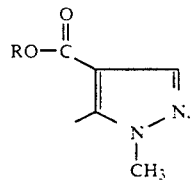

where
 R represents $C_1$-$C_4$-alkyl, or
$R^1$ represents the radical

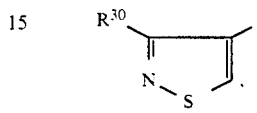

where
 $R^{30}$ represents hydrogen, chlorine, methyl, ethyl, methoxycarbonyl or ethoxycarbonyl; in which furthermore $R^2$ represents hydrogen or for the group —$SO_2$—$R^1$, where
 $R^1$ has the meaning indicated above as being particularly preferred, $R^3$ represents hydrogen, methyl, ethyl, propyl, isopropyl, trifluoromethyl, cyclopropyl, benzyl, phenyl, t-butyl, s-butyl, i-butyl, n-butyl, methoxy or methylthio, $R^4$ represents hydrogen, fluorine, chlorine, bromine, methyl, trifluoromethyl, methoxy, ethoxy, difluoromethoxy, methylthio, ethylthio, amino, methylamino, ethylamino, dimethylamino or diethylamino, X represents nitrogen or a CH group, Y represents nitrogen or a $CR^5$ group where
 $R^5$ represents hydrogen, fluorine, chlorine or methyl, and Z represents nitrogen or a $CR^6$ group where
 $R^6$ represents hydrogen, fluorine, chlorine, bromine, methyl, ethyl, methoxy, ethoxy, propoxy, isopropoxy, difluoromethoxy, methylthio, ethylthio, methylamino, ethylamino, dimethylamino or diethylamino.

The invention furthermore preferably relates to salts of compounds of the formula (I)

α) with proton acids, such as, for example, hydrochloric acid, sulphuric acid, phosphoric acid, methanesulphonic acid, benzene- or p-toluenesulphonic acid, or naphthalene-mono- or -di-sulphonic acids, or β) with bases, such as, for example, sodium hydroxide, potassium hydroxide, calcium hydroxide, sodium hydride, potassium hydride, calcium hydride, sodium amide, potassium amide, calcium amide, sodium carbonate, potassium carbonate or calcium carbonate, sodium $C_1$-$C_4$-alkanoxides or potassium $C_1$-$C_4$-alkanoxides, ammonia, $C_1$-$C_4$-alkylamines, di-($C_1$-$C_4$-alkyl)-amines or tri-($C_1$-$C_4$-alkyl)-amines.

If, for example, 4-amino-5-methyl-2-(4,6-dimethoxy-s-triazin-2-yl)-2,4-dihydro-3H-1,2,4-triazol-3-one and 2-fluoro-benzenesulphonyl chloride (at least two mole equivalents) are used as starting substances in process (a) according to the invention, the course of the reaction in process (a) according to the invention can be outlined by the following equation:

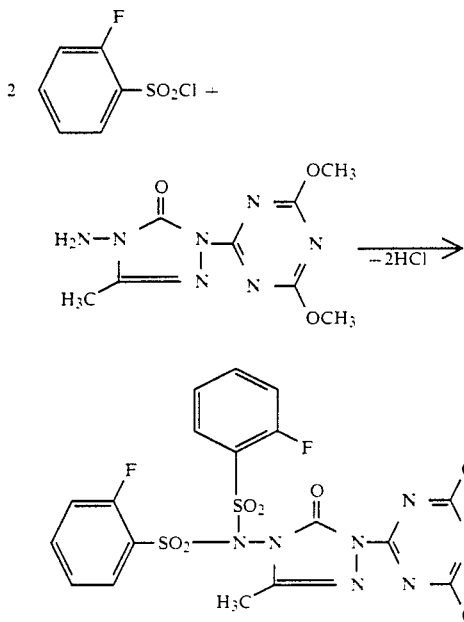

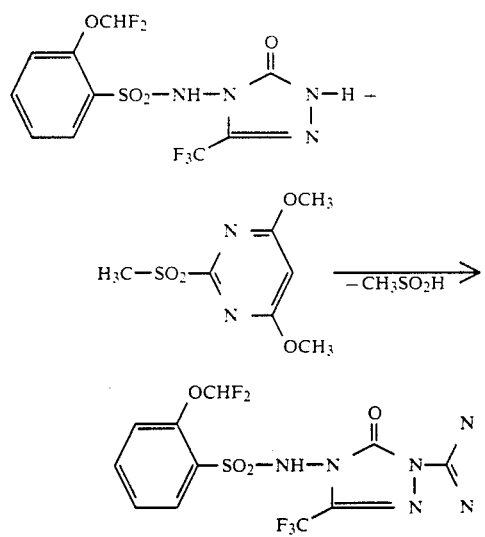

If, for example, 4-(2-difluormethoxy-phenylsulphonylamino)-5-trifluormethyl-2,4-dihydro-3H-1,2,4-triazol-3-one and 4,6-dimethoxy-2-methylsulphonyl-pyrimidine are used as starting substances in process (b) according to the invention, the course of the reaction in process (b) according to the invention can be outlined by the following equation:

Formula (II) provides a general definition of the substituted aminotriazolinones to be used as starting substances in the process (a) according to the invention for the preparation of compounds of the formula (I).

In formula (II), $R^3$, $R^4$, X, Y and Z preferably, or in particular, have those meanings which have already been mentioned above in connection with the description of the compounds of the formula (I) according to the invention as being preferred, or particularly preferred, for $R^3$, $R^4$, X, Y and Z.

Examples of the starting substances of the formula (II) are listed in Table 1 below.

TABLE 1

Examples of the starting substances of the formula (II)

| $R^3$ | $R^4$ | X | Y | Z |
|---|---|---|---|---|
| H | CH₃ | N | CH | C—CH₃ |
| H | CH₃ | N | CH | C—OCH₃ |
| H | CH₃ | N | CH | C—OC₂H₅ |
| H | OCH₃ | N | CH | C—OCH₃ |
| H | OCH₃ | N | CH | C—Cl |
| H | H | N | CH | C—CH₃ |
| H | CF₃ | N | CH | C—CH₃ |
| H | CF₃ | N | CH | C—OCH₃ |
| H | CF₃ | N | CH | C—CF₃ |
| H | OCH₃ | N | CH | C—OCHF₂ |
| H | CH₃ | N | CH | C—OCHF₂ |
| H | OCHF₂ | N | CH | C—OCHF₂ |
| H | CH₃ | N | N | C—OCH₃ |
| H | OCH₃ | N | N | C—OCH₃ |
| H | OCH₃ | N | N | C—Cl |
| H | C₂H₅ | N | CH | C—OCH₃ |
| H | C₂H₅ | N | N | C—OCH₃ |
| CH₃ | CH₃ | N | CH | C—CH₃ |
| CH₃ | CH₃ | N | CH | C—OCH₃ |
| CH₃ | OCH₃ | N | CH | C—OCH₃ |
| CH₃ | OCH₃ | N | CH | C—Cl |
| CH₃ | OCHF₂ | N | CH | C—OCHF₂ |
| CH₃ | H | N | CH | C—CH₃ |
| CH₃ | CF₃ | N | CH | C—CH₃ |
| CH₃ | CF₃ | N | CH | C—OCH₃ |
| CH₃ | CF₃ | N | CH | C—CF₃ |
| CH₃ | OCH₃ | N | CH | C—OCHF₂ |
| CH₃ | Cl | N | CH | C—OCHF₂ |
| CH₃ | CH₃ | N | CH | C—OCHF₂ |
| CH₃ | NH—CH₃ | N | CH | C—OCH₃ |
| CH₃ | CH₃ | N | N | C—CH₃ |
| CH₃ | CH₃ | N | N | C—OCH₃ |
| CH₃ | OCH₃ | N | N | C—OCH₃ |
| CH₃ | C₂H₅ | N | CH | C—OCH₃ |
| CH₃ | CH₃ | N | N | C—OC₂H₅ |
| CH₃ | C₂H₅ | N | N | C—OCH₃ |
| CH₃ | CH₃ | N | N | C—Cl |
| CH₃ | CH₃ | CH | N | C—CH₃ |
| CH₃ | OCH₃ | CH | N | C—OCH₃ |
| CH₃ | CH₃ | N | CH | C—SCH₃ |
| H | CH₃ | N | CH | C—N(CH₃)₂ |
| H | OCH₃ | N | CH | C—SCH₃ |
| H | OCH₃ | N | N | C—NHC₂H₅ |
| H | OC₂H₅ | N | N | C—NHCH₃ |
| H | CH₃ | CH | CH | C—CH₃ |
| OCH₃ | CH₃ | N | CH₃ | C—CH₃ |
| OCH₃ | CH₃ | N | CH | C—OCH₃ |
| OCH₃ | OCH₃ | N | CH | C—OCH₃ |
| OCH₃ | OCH₃ | N | CH | C—Cl |
| OCH₃ | H | N | CH | C—CH₃ |
| OCH₃ | CF₃ | N | CH | C—OCH₃ |
| OCHF₂ | OCH₃ | N | CH | C—OCHF₂ |
| OCH₃ | CH₃ | N | CH | C—OCHF₂ |
| OCH₃ | CH₃ | N | N | C—CH₃ |
| OCH₃ | CH₃ | N | N | C—OCH₃ |
| OCH₃ | OCH₃ | N | N | C—OCH₃ |
| OCH₃ | C₂H₅ | N | CH | C—OCH₃ |
| OCH₃ | C₂H₅ | N | N | C—OCH₃ |
| SCH₃ | CH₃ | N | CH | C—CH₃ |
| OCH₃ | CH₃ | N | N | C—OC₂H₅ |
| SCH₃ | CH₃ | N | CH | C—OCH₃ |
| SCH₃ | CH₃ | N | CH | C—OC₂H₅ |
| SCH₃ | OCH₃ | N | CH | C—OCH₃ |
| SCH₃ | OCH₃ | N | CH | C—Cl |
| SCH₃ | H | N | CH | C—CH₃ |
| SCH₃ | CF₃ | N | CH | C—CF₃ |
| SCH₃ | CF₃ | N | CH | C—OCH₃ |
| SCH₃ | CF₃ | N | CH | C—CH₃ |
| SCH₃ | OCH₃ | N | CH | C—OCHF₂ |
| SCH₃ | CH₃ | N | CH | C—OCHF₂ |
| SCH₃ | OCHF₂ | N | CH | C—OCHF₂ |
| SCH₃ | NHCH₃ | N | CH | C—OCH₃ |
| SCH₃ | CH₃ | N | N | C—CH₃ |
| SCH₃ | CH₃ | N | N | C—OCH₃ |
| SCH₃ | OCH₃ | N | N | C—OCH₃ |
| SCH₃ | OCH₃ | N | N | C—Cl |
| SCH₃ | C₂H₅ | N | CH | C—OCH₃ |
| SCH₃ | C₂H₅ | N | N | C—OCH₃ |
| SCH₃ | OCH₃ | N | N | C—NH—C₂H₅ |

TABLE 1-continued

Examples of the starting substances of the formula (II)

| R³ | R⁴ | X | Y | Z |
|---|---|---|---|---|
| SCH₃ | OC₂H₅ | N | N | C—NH—CH₃ |
| C₂H₅ | CH₃ | N | CH | C—CH₃ |
| C₂H₅ | CH₃ | N | CH | C—OCH₃ |
| C₂H₅ | CH₃ | N | CH | C—OC₂H₅ |
| C₂H₅ | OCH₃ | N | CH | C—OCH₃ |
| C₂H₅ | OCH₃ | N | CH | C—Cl |
| C₂H₅ | H | N | CH | C—CH₃ |
| C₂H₅ | CF₃ | N | CH | C—CH₃ |
| C₂H₅ | CF₃ | N | CH | C—OCH₃ |
| C₂H₅ | CF₃ | N | CH | C—CF₃ |
| C₂H₅ | OCH₃ | N | CH | C—OCHF₂ |
| C₂H₅ | CH₃ | N | CH | C—OCHF₂ |
| C₂H₅ | OCHF₂ | N | CH | C—OCHF₂ |
| C₂H₅ | NHCH₃ | N | CH | C—OCH₃ |
| C₂H₅ | CH₃ | N | N | C—CH₃ |
| C₂H₅ | CH₃ | N | N | C—OCH₃ |
| C₂H₅ | OCH₃ | N | N | C—OCH₃ |
| C₂H₅ | C₂H₅ | N | N | C—OCH₃ |
| C₂H₅ | CH₃ | N | N | C—N(CH₃)₂ |
| C₂H₅ | OCH₃ | N | N | C—NHC₂H₅ |
| C₂H₅ | OC₂H₅ | N | N | C—NHCH₃ |
| C₃H₇-n | CH₃ | N | CH | C—CH₃ |
| C₃H₇-n | CH₃ | N | CH | C—OCH₃ |
| C₃H₇-n | CH₃ | N | CH | C—OC₂H₅ |
| C₃H₇-n | OCH₃ | N | CH | C—OCH₃ |
| C₃H₇-n | OCH₃ | N | CH | C—Cl |
| C₃H₇-n | H | N | CH | C—CH₃ |
| C₃H₇-n | CF₃ | N | CH | C—CH₃ |
| C₃H₇-n | CF₃ | N | CH | C—OCH₃ |
| C₃H₇-n | CF₃ | N | CH | C—CF₃ |
| C₃H₇-n | OCH₃ | N | CH | C—OCHF₂ |
| C₃H₇-n | CH₃ | N | CH | C—OCHF₂ |
| C₃H₇-n | OCHF₂ | N | CH | C—OCHF₂ |
| C₃H₇-n | NHCH₃ | N | CH | C—OCH₃ |
| C₃H₇-n | CH₃ | N | N | C—CH₃ |
| C₃H₇-n | CH₃ | N | N | C—OCH₃ |
| C₃H₇-n | OCH₃ | N | N | C—OCH₃ |
| C₃H₇-n | C₂H₅ | N | N | C—OCH₃ |
| C₃H₇-n | CH₃ | N | N | C—N(CH₃)₂ |
| C₃H₇-n | OCH₃ | N | N | C—NHC₂H₅ |
| C₃H₇-n | OC₂H₅ | N | N | C—NHCH₃ |
| C₃H₇-i | CH₃ | N | CH | C—CH₃ |
| C₃H₇-i | CH₃ | N | CH | C—OCH₃ |
| C₃H₇-i | CH₃ | N | CH | C—OC₂H₅ |
| C₃H₇-i | OCH₃ | N | CH | C—OCH₃ |
| C₃H₇-i | OCH₃ | N | CH | C—Cl |
| C₃H₇-i | H | N | CH | C—CH₃ |
| C₃H₇-i | CF₃ | N | CH | C—CH₃ |
| C₃H₇-i | CF₃ | N | CH | C—OCH₃ |
| C₃H₇-i | CF₃ | N | CH | C—CF₃ |
| C₃H₇-i | OCH₃ | N | CH | C—OCHF₂ |
| C₃H₇-i | CH₃ | N | CH | C—OCHF₂ |
| C₃H₇-i | OCHF₂ | N | CH | C—OCHF₂ |
| C₃H₇-i | NHCH₃ | N | CH | C—OCH₃ |
| C₃H₇-i | CH₃ | N | N | C—CH₃ |
| C₃H₇-i | CH₃ | N | N | C—OCH₃ |
| C₃H₇-i | OCH₃ | N | N | C—OCH₃ |
| C₃H₇-i | C₂H₅ | N | N | C—OCH₃ |
| C₃H₇-i | CH₃ | N | N | C—N(CH₃)₂ |
| C₃H₇-i | OCH₃ | N | N | C—NHC₂H₅ |
| C₃H₇-i | OC₂H₅ | N | N | C—NHCH₃ |
| c-C₃H₅ | CH₃ | N | CH | C—CH₃ |
| c-C₃H₅ | CH₃ | N | CH | C—OCH₃ |
| c-C₃H₅ | CH₃ | N | CH | C—OC₂H₅ |
| c-C₃H₅ | OCH₃ | N | CH | C—OCH₃ |
| c-C₃H₅ | OCH₃ | N | CH | C—Cl |
| c-C₃H₅ | H | N | CH | C—CH₃ |
| c-C₃H₅ | CF₃ | N | CH | C—CH₃ |
| c-C₃H₅ | CF₃ | N | CH | C—OCH₃ |
| c-C₃H₅ | CF₃ | N | CH | C—CF₃ |
| c-C₃H₅ | OCH₃ | N | CH | C—OCHF₂ |
| c-C₃H₅ | CH₃ | N | CH | C—OCHF₂ |
| c-C₃H₅ | OCHF₂ | N | CH | C—OCHF₂ |
| c-C₃H₅ | NHCH₃ | N | CH | C—OCH₃ |
| c-C₃H₅ | CH₃ | N | N | C—CH₃ |
| c-C₃H₅ | CH₃ | N | N | C—OCH₃ |
| c-C₃H₅ | OCH₃ | N | N | C—OCH₃ |
| c-C₃H₅ | C₂H₅ | N | N | C—OCH₃ |
| c-C₃H₅ | CH₃ | N | N | C—N(CH₃)₂ |
| c-C₃H₅ | OCH₃ | N | N | C—NHC₂H₅ |
| c-C₃H₅ | OC₂H₅ | N | N | C—NHCH₃ |
| C₄H₉-n | CH₃ | N | CH | C—CH₃ |
| C₄H₉-n | CH₃ | N | CH | C—OCH₃ |
| C₄H₉-n | CH₃ | N | CH | C—OC₂H₅ |
| C₄H₉-n | OCH₃ | N | CH | C—OCH₃ |
| C₄H₉-n | OCH₃ | N | CH | C—Cl |
| C₄H₉-n | CH₃ | N | CH | C—CH₃ |
| C₄H₉-n | CF₃ | N | CH | C—CH₃ |
| C₄H₉-n | CF₃ | N | CH | C—OCH₃ |
| C₄H₉-n | CF₃ | N | CH | C—CF₃ |
| C₄H₉-n | OCH₃ | N | CH | C—OCHF₂ |
| C₄H₉-n | CH₃ | N | CH | C—OCHF₂ |
| C₄H₉-n | OCHF₂ | N | CH | C—OCHF₂ |
| C₄H₉-n | NHCH₃ | N | CH | C—OCH₃ |
| C₄H₉-n | CH₃ | N | N | C—CH₃ |
| C₄H₉-n | CH₃ | N | N | C—OCH₃ |
| C₄H₉-n | OCH₃ | N | N | C—OCH₃ |
| C₄H₉-n | C₂H₅ | N | N | C—OCH₃ |
| C₄H₉-n | CH₃ | N | N | C—N(CH₃)₂ |
| C₄H₉-n | OCH₃ | N | N | C—NHC₂H₅ |
| C₄H₉-n | OC₂H₅ | N | N | C—NHCH₃ |
| C₄H₉-s | CH₃ | N | CH | C—CH₃ |
| C₄H₉-s | CH₃ | N | CH | C—OCH₃ |
| C₄H₉-s | CH₃ | N | CH | C—OC₂H₅ |
| C₄H₉-s | OCH₃ | N | CH | C—OCH₃ |
| C₄H₉-s | OCH₃ | N | CH | C—Cl |
| C₄H₉-s | H | N | CH | C—CH₃ |
| C₄H₉-s | CF₃ | N | CH | C—CH₃ |
| C₄H₉-s | CF₃ | N | CH | C—OCH₃ |
| C₄H₉-s | CF₃ | N | CH | C—CF₃ |
| C₄H₉-s | OCH₃ | N | CH | C—OCHF₂ |
| C₄H₉-s | CH₃ | N | CH | C—OCHF₂ |
| C₄H₉-s | OCHF₂ | N | CH | C—OCHF₂ |
| C₄H₉-s | NHCH₃ | N | CH | C—OCH₃ |
| C₄H₉-s | CH₃ | N | N | C—CH₃ |
| C₄H₉-s | CH₃ | N | N | C—OCH₃ |
| C₄H₉-s | OCH₃ | N | N | C—OCH₃ |
| C₄H₉-s | C₂H₅ | N | N | C—OCH₃ |

TABLE 1-continued

Examples of the starting substances of the formula (II)

| R³ | R⁴ | X | Y | Z |
|---|---|---|---|---|
| C₄H₉-s | CH₃ | N | N | C—N(CH₃)₂ |
| C₄H₉-s | OCH₃ | N | N | C—NHC₂H₅ |
| C₄H₉-s | OC₂H₅ | N | N | C—NHCH₃ |
| C₄H₉-i | CH₃ | N | CH | C—CH₃ |
| C₄H₉-i | CH₃ | N | CH | C—OCH₃ |
| C₄H₉-i | CH₃ | N | CH | C—OC₂H₅ |
| C₄H₉-i | OCH₃ | N | CH | C—OCH₃ |
| C₄H₉-i | OCH₃ | N | CH | C—Cl |
| C₄H₉-i | H | N | CH | C—CH₃ |
| C₄H₉-i | CF₃ | N | CH | C—CH₃ |
| C₄H₉-i | CF₃ | N | CH | C—OCH₃ |
| C₄H₉-i | CF₃ | N | CH | C—CF₃ |
| C₄H₉-i | OCH₃ | N | CH | C—OCHF₂ |
| C₄H₉-i | CH₃ | N | CH | C—OCHF₂ |
| C₄H₉-i | OCHF₂ | N | CH | C—OCHF₂ |
| C₄H₉-i | NHCH₃ | N | CH | C—OCH₃ |
| C₄H₉-i | CH₃ | N | N | C—CH₃ |
| C₄H₉-i | CH₃ | N | N | C—OCH₃ |
| C₄H₉-i | OCH₃ | N | N | C—OCH₃ |
| C₄H₉-i | C₂H₅ | N | N | C—OCH₃ |
| C₄H₉-i | CH₃ | N | N | C—N(CH₃)₂ |
| C₄H₉-i | OCH₃ | N | N | C—NHC₂H₅ |
| C₄H₉-i | OC₂H₅ | N | N | C—NHCH₃ |
| C₄H₉-t | CH₃ | N | CH | C—CH₃ |
| C₄H₉-t | CH₃ | N | CH | C—OCH₃ |
| C₄H₉-t | CH₃ | N | CH | C—OC₂H₅ |
| C₄H₉-t | OCH₃ | N | CH | C—OCH₃ |
| C₄H₉-t | OCH₃ | N | CH | C—Cl |
| C₄H₉-t | H | N | CH | C—CH₃ |
| C₄H₉-t | CF₃ | N | CH | C—CH₃ |
| C₄H₉-t | CF₃ | N | CH | C—OCH₃ |
| C₄H₉-t | CF₃ | N | CH | C—CF₃ |
| C₄H₉-t | OCH₃ | N | CH | C—OCHF₂ |
| C₄H₉-t | CH₃ | N | CH | C—OCHF₂ |
| C₄H₉-t | OCHF₂ | N | CH | C—OCHF₂ |
| C₄H₉-t | NHCH₃ | N | CH | C—OCH₃ |
| C₄H₉-t | CH₃ | N | N | C—CH₃ |
| C₄H₉-t | CH₃ | N | N | C—OCH₃ |
| C₄H₉-t | OCH₃ | N | N | C—OCH₃ |
| C₄H₉-t | C₂H₅ | N | N | C—OCH₃ |
| C₄H₉-t | CH₃ | N | N | C—N(CH₃)₂ |
| C₄H₉-t | OCH₃ | N | N | C—NHC₂H₅ |
| C₄H₉-t | OC₂H₅ | N | N | C—NHCH₃ |
| CF₃ | CH₃ | N | CH | C—CH₃ |
| CF₃ | CH₃ | N | CH | C—OCH₃ |
| CF₃ | CH₃ | N | CH | C—OC₂H₅ |
| CF₃ | OCH₃ | N | CH | C—OCH₃ |
| CF₃ | OCH₃ | N | CH | C—Cl |
| CF₃ | H | N | CH | C—CH₃ |
| CF₃ | CF₃ | N | CH | C—CH₃ |
| CF₃ | CF₃ | N | CH | C—OCH₃ |
| CF₃ | CF₃ | N | CH | C—CF₃ |
| CF₃ | OCH₃ | N | CH | C—OCHF₂ |
| CF₃ | CH₃ | N | CH | C—OCHF₂ |
| CF₃ | OCHF₂ | N | CH | C—OCHF₂ |
| CF₃ | NHCH₃ | N | CH | C—OCH₃ |
| CF₃ | CH₃ | N | N | C—CH₃ |
| CF₃ | CH₃ | N | N | C—OCH₃ |
| CF₃ | OCH₃ | N | N | C—OCH₃ |
| CF₃ | C₂H₅ | N | N | C—OCH₃ |
| CF₃ | CH₃ | N | N | C—N(CH₃)₂ |
| CF₃ | OCH₃ | N | N | C—NHC₂H₅ |
| CF₃ | OC₂H₅ | N | N | C—NHCH₃ |
| C₆H₅ | CH₃ | N | CH | C—CH₃ |
| C₆H₅ | CH₃ | N | CH | C—OCH₃ |
| C₆H₅ | OCH₃ | N | CH | C—OCH₃ |
| C₆H₅ | OCH₃ | N | CH | C—Cl |
| C₆H₅ | CH₃ | N | N | C—OCH₃ |
| C₆H₅ | OCH₃ | N | N | C—OCH₃ |
| CH₂C₆H₅ | CH₃ | N | CH | C—CH₃ |
| CH₂C₆H₅ | CH₃ | N | CH | C—OCH₃ |
| CH₂C₆H₅ | OCH₃ | N | CH | C—OCH₃ |
| CH₂C₆H₅ | OCH₃ | N | CH | C—Cl |
| CH₂C₆H₅ | CH₃ | N | N | C—OCH₃ |
| CH₂C₆H₅ | OCH₃ | N | N | C—OCH₃ |

The substituted aminotriazolinones of the formula (II), which are to be used as starting substances in process (a), were hitherto unknown from the literature.

The new compounds of the formula (II) are obtained when
(α) aminotriazolinones of the general formula (VI)

(VI)

in which
R³ has the abovementioned meaning,
are reacted at temperatures between 20° C. and 150° C., if appropriate, with carbonyl compounds of the general formula (VII)

(VII)

in which
A¹ represents hydrogen or alkyl and
A² represents alkyl or aryl,
if appropriate in the presence of a catalyst, such as, for example, sulphuric acid, methanesulphonic acid or p-toluenesulphonic acid, and if appropriate in the presence of a diluent, such as, for example, methylene chloride, toluene, xylene, methanol, ethanol or isopropanol,
the alkylideneaminotriazolinones (some of which are new) formed in this process of the general formula (VIII)

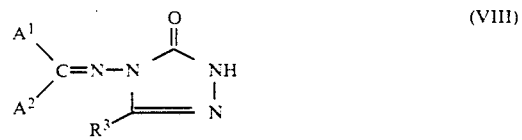

(VIII)

in which
A¹, A² and R³ have the abovementioned meanings, are, if appropriate, isolated and/or reacted virtually in situ, that is to say after concentrating the reaction mixture, with azines of the general formula (V)

(V)

in which
R⁴, X, Y and Z have the abovementioned meanings and
Q¹ represents halogen, benzylsulphonyl or alkylsulphonyl,
if appropriate in the presence of an acid acceptor, such as, for example, potassium carbonate, and if appropriate in the presence of a diluent, such as, for example, acetonitrile or dimethylformamide, at temperatures between 0° C. and 150° C.
and the (new) substituted alkylideneaminotriazolinones formed in this process, of the general formula (IX)

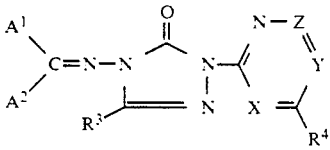

(IX)

in which

A$^1$, A$^2$, A$^3$, R$^4$, X, Y and Z have the abovementioned meanings, are hydrolyzed in a customary manner, for example by reacting them with water, if appropriate in the presence of an organic solvent, such as, for example, methanol, ethanol, isopropanol or dioxane, and if appropriate in the presence of an acid, such as, for example, hydrochloric acid or sulphuric acid, at temperatures between 20° C. and 100° C. to give the compounds of the formula (II); or when (β) oxadiazolones of the general formula (X)

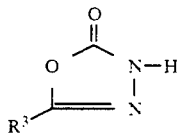

(X)

in which

R$^3$ has the abovementioned meaning, are reacted with azines of the general formula (V) -aboveif appropriate in the presence of an acid acceptor, such as, for example, potassium carbonate, and if appropriate in the presence of a diluent, such as, for example, acetonitrile, dioxane or dimethylformamide, at temperatures between 0° C. and 150° C.

and the (new) substituted oxadiazolones formed in this process, of the general formula (XI)

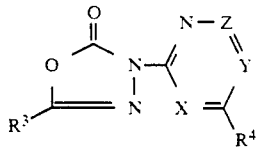

(XI)

in which

R$^3$, R$^4$, X, Y and Z have the abovementioned meanings, are reacted with hydrazine or hydrazine hydrate at temperatures between 0° C. and 150° C.

Some of the compounds of the formula (II) can be prepared using a synthesis route similar to the one described under (α) but without introducing protective groups using carbonyl compounds of the formula (VII), that is to say by directly reacting compounds of the formula (VI) with compounds of the formula (V) under the reaction conditions indicated under (α).

Formula (VI) provides a general definition of the aminotriazolinones, which are required as intermediates. In formula (VI), R$^3$ preferably, or in particular, has the meaning which has already been indicated above in connection with the description of the compounds of the formula (I) according to the invention as being preferred, or particularly preferred, for R$^3$.

Example of the compounds of the formula (VI) which may be mentioned are: 4-amino-2,4-dihydro-3-H-1,2,4-triazol-3-one, 4-amino-5-methyl-2,4-dihydro-3H-1,2,4-triazol-3-one, 4-amino-5-methoxy-2,4-dihydro-3H-1,2,4-triazol-3-one, 4-amino-5-methylthio-2,4-dihydro-3H-1,2,4-triazol-3-one, 4amino-5-ethyl-2,4-dihydro-3H-1,2,4-triazol-3-one, 4-amino-5-propyl-2,4-dihydro-3H-1,2,4-triazol-3-one, 4-amino-5-cyclopropyl-2,4-dihydro-3H-1,2,4-triazol-3-one, 4-amino-5-isopropyl-2,4-dihydro-3H-1,2,4-triazol-3-one, 4-amino-5-butyl-2,4-dihydro-3H-1,2,4-triazol-3-one, 4-amino-5-isobutyl-2,4-dihydro-3H-1,2,4-triazol-3-one and 4-amino-5-tert.-butyl-2,4-dihydro-3H-1,2,4-triazol-3-one.

The aminotriazolinones of the formula (VI) are known and/or can be prepared by processes known per se (cf. Chem. Ber. 98 (1965), 3025–3033; J.Heterocycl. Chem. 21 (1984), 1769–1774; Doga: Kim. Ser. 10 (1986), 34–39 -quoted in Chem. Abstracts 106: (1987), 138338e).

Formula (VII) provides a definition of the carbonyl compounds also required as intermediates.

In formula (VII),

A$^1$ preferably represents hydrogen or methyl and

A$^2$ preferably represents methyl, ethyl, propyl, isopropyl, butyl, isobutyl or phenyl.

Examples of the compounds of the formula (VII) which may be mentioned are: acetone, methyl ethyl ketone, methyl propyl ketone, methyl isopropyl ketone, methyl butyl ketone, methyl isobutyl ketone and benzaldehyde.

The intermediates of the formula (VII) are known chemicals for organic synthesis.

Formula (V) provides a general definition of the azines also required as intermediates. In formula (V), R$^4$, X, Y and Z preferably, or in particular, have those meanings which have already been mentioned above in connection with the description of the compounds of the formula (I) according to the invention as being preferred, or particularly preferred, for R$^4$, X, Y and Z, and Q$^1$ preferably represents fluorine, chlorine, bromine, benzylsulphonyl or C$_1$-C$_4$-alkylsulphonyl, in particular represents chlorine or methylsulphonyl.

Examples of the compounds of the formula (V) which may be mentioned are: 2-chloro-, 2-benzylsulphonyl- and 2-methylsulphonyl-4,6-dimethyl-pyrimidine, -4-methyl-6-methoxy-pyrimidine, -4,6-dimethoxy-pyrimidine, -4-methyl-6-ethoxy-pyrimidine, -4-chloro-6methoxy-pyrimidine, -4-methyl-pyrimidine, -4-chloro-6-methyl-pyrimidine, -4-trifluoromethyl-6-methoxy-pyrimidine, -4-methoxy-6-difluoromethoxy-pyrimidine, -4-methyl-6-difluoromethoxy-pyrimidine, -4,6-bis-difluoromethoxy-pyrimidine, -4-chloro-6-ethoxy-pyrimidine, -4-chloro-6-difluoromethoxy-pyrimidine, -4-chloro-6-ethoxy-pyrimidine, -4-chloro-6-difluoromethoxy-pyrimidine, -4-methoxy-5-methyl-pyrimidine, -4-trifluoromethyl-6-difluoromethoxy-pyrimidine, -4,6-diethoxy-pyrimidine, -4,5-dichloro-6-methyl-pyrimidine, -4-methyl-5-chloro-6methoxy-pyrimidine, -4,6-dichloro-pyrimidine, -4-ethyl-6-methoxy-pyrimidine, -5chloro-4,6-dimethoxy-pyrimidine, -4-methoxy-6-methylamino-pyrimidine and -4,6-bis-trifluoromethyl-pyrimidine, furthermore 2-chloro-4,6-dimethyl-s-triazine, 2-chloro-4-methyl-6-methoxy-s-triazine, 2-chloro-4,6-dimethoxy-s-triazine, 2,4-dichloro-6-methoxy-s-triazine, 2-chloro-4-ethyl-6-methoxy-s-triazine, 2-chloro-4-methyl-6-methoxy-s-triazine, 2-chloro-4-ethoxy-6-methylamino-s-triazine, 2-chloro-4-methoxy-6-methylamino-s-triazine, 2-chloro-4-methoxy-6-ethylamino-s-triazine and 2-chloro-4-ethoxy-6-ethylamino-s-triazine.

The azines of the formula (V) are known and/or can be prepared by processes known per se (cf., J. Chem. Soc. 1957, 1830, 1833; J. Org. Chem. 26 (1961), 792; U.S. Pat. No. 3,308,119 and U.S. Pat. No. 4,711,959).

Formula (X) provides a general definition of the oxadiazolones also to be used as intermediates. In formula (X), $R^3$ preferably, or in particular, has the meaning which has already been mentioned above in connection with the description of the compounds of the formula (I) according to the invention as being preferred, or particularly preferred, for $R^3$.

Examples of the compounds of the formula (X) which may be mentioned are: 1,3,4-oxidiazol-2(3H)-one, 5-methyl-1,3,4-oxadiazol-2(3H)-one, 5-ethyl-1,3,4-oxadiazol-2(3H)-one, 5-propyl-1,3,4-oxadiazol-2(3H)-one, 5-isopropyl-1,3,4-oxadiazol-2(3H)-one, 5-butyl-1,3,4-oxadiazol-2(3H)-one, 5-trifluoromethyl-1,3,4-oxadiazol-2(3H)-one, 5-tert.-butyl-1,3,4-oxadiazol-2(3H)-one, 5-cyclopropyl-1,3,4-oxadiazol-2(3H)-one, 5-methoxy-1,3,4-oxadiazol-2(3H)-one and 5-methylthio-1,3,4-oxidiazol-2(3H)-one.

The oxadiazolones of the formula (X) are known and/or can be prepared by processes known per se (cf. Helv. Chim. Acta 55 (1955), 1174-1178).

Formula (III) provides a general definition of the sulphonyl halides or sulphonic anhydrides also to be used as starting substances in process (a) according to the invention for the preparation of the new compounds of the formula (I). In formula (III), $R^1$ preferably, or in particular, has the meaning which has been indicated above in connection with the description of the compounds of the formula (I) according to the invention as being preferred, or particularly preferred, and Q preferably represents chlorine.

Starting substances of the formula (III) which may be mentioned by way of example are: benzenesulphonyl chloride, 2-chloro-, 3-chloro-, 4-chloro-, 2,5-dichloro-, 2-fluoro-, 4-fluoro-, 2-bromo-, 4-bromo-, 2-cyano-, 2-nitro-, 4-nitro-, 2-methyl-, 4-methyl, 2-chloromethyl-, 2-trifluoromethyl-, 2-methoxy-, 4methoxy-, 2-(2-methoxy-ethoxy)-, 2-methylsulphonyl-, 2--isopropoxy-carbonyl-, 2-chloro-6-methyl-, 2-bromo-6-methyl-, 2-methylthio-, 2-trifluoromethylthio-, 2-difluoromethylthio-, 2-cyclopropyloxcarbonyl-, 2-phenoxy-, 2-difluoromethoxy-, 2-trifluoromethoxy-, 2-(2-chloroethoxy)-, 2-methylthiomethyl-, 2-dimethylaminosulphonyl-, 2-phenyl-, 2-methoxycarbonyl-, 2-ethoxcarbonyl-, 2dimethylaminocarbonyl- and 2-diethylaminocarbonyl-benzenesulphonyl chloride and (2-chloro-phenyl)-, (2-cyano-phenyl)-, (2-methoxycarbonylphenyl)-, (2-trifluoromethoxy-phenyl)- and (2-difluoro methoxy-phenyl)-methanesulphonyl chloride, furthermore 1-methyl-4-methoxycarbonyl-pyrazole-5-sulphonyl chloride, 1-methyl-4-ethoxycarbonyl-pyrazole-5-sulphonyl chloride, 1-methyl-4-bromo-pyrazole-5-sulphonyl chloride, 2-methoxycarbonyl-thiophene-3-sulphonyl chloride, 3-trifluoromethyl-pyridine-2-sulphonyl chloride 3-dimethylamino-carbonyl-pyridine-2-sulphonyl chloride, 3-dimethylaminocarbonyl-6-methyl-pyridine-2-sulphonyl chloride, 3-dimethylaminocarbonyl-6-chloro-pyridine-2-sulphonyl chloride and 1-(iso)quinolinyl-4-ethoxycarbonyl-pyrazole-5-sulphonyl chloride.

The sulphonyl halides or sulphonic anhydrides of the formula (III) are known and/or can be prepared by processes known per se (cf. J. Org. Chem. 33 (1968), 2104; J. Org. Chem. 25 (1960), 1824; DE-AS (German Published Specification) 2,308,262; EP-OS (European Published Specification) 23,140, 23,141, 23,422, 35,893, 48,143, 51,466, 64,322, 70,041, 44,808 and 44,809; U.S. Pat. Nos. 2,929,820, 4,282,242; 4,348,220 and 4,372,778 and Angew. Chem. 93 (1981), 151).

Process (a) according to the invention for the preparation of the new compounds of the formula (I) is preferably carried out using diluents. Suitable diluents for this process are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and dimethyl sulphoxide, tetramethylene sulphone and hexamethylphosphoric triamide and pyridine.

Acid acceptors which can be employed in process (a) according to the invention are all acid-binding agents which can customarily be used for reactions of this type. Alkali metal hydroxides, such as, for example, sodium hydroxide and potassium hydroxide, alkaline earth metal hydroxides, such as, for example, calcium hydroxide, alkali metal carbonates and alkali metal alkoxides, such as sodium carbonate and potassium carbonate, sodium tert.-butoxide and potassium tert.-butoxide, furthermore aliphatic, aromatic or heterocyclic amines, for example triethylamine, trimethylamine, dimethylaniline, dimethylbenzylamine, pyridine, picoline, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO), are preferably suitable.

In process (a) according to the invention, the reaction temperatures can be varied within a relatively wide range. In general, the reaction is carried out at temperatures between $-50°$ C. and $+50°$ C., preferably at temperatures between $-40°$ C. and $+40°$ C.

For carrying out process (a) according to the invention, between 1 and 5 moles, preferably between 1 and 4 moles, of sulphonyl halide or sulphonic anhydride of the formula (III) are generally employed per mole of aminotriazolinone of the formul (II). In the case where disulphonylated compounds of the formula (I, $R^2 = -SO_2 - R^1$) are to be prepared in a one-pot reaction, at least 2 moles of sulphonyl halide or sulphonic anhydride (III) are to be employed per mole of aminotriazolinone (II).

The reactants can be combined in any desired sequence. In a preferred embodiment of process (a) according to the invention, the starting substances of the formula (II) and (III) are stirred at room temperature with a diluent, and the acid acceptor is slowly metered into this mixture, if appropriate after cooling. The reaction mixture is then stirred until the reaction is complete.

Working up can be carried out in a customary manner, for example by washing with water—if approppriate after concentrating and/or diluting the mixture witha virtually water-immiscible organic solvent, such as, for example, methylene chloride—drying and filtering the mixture, and carefully distilling off the solvent from the filtrate. The crude product, which remains in the residue, can be purified further in a customary manner, for example by column chromatography and/or by recrystallization.

The compounds which can be obtained as described above of the formula (I) in which $R^2$ represents the group $—SO_2—R^1$ can be reacted to give compounds of the formula (I) in which $R^2$ represents hydrogen by reaction with desulphonylating agents, if appropriate in the presence of diluents.

In this connection, desulphonylating agents are taken to mean substances which can eliminate a sulphonyl group from N,N-bis-sulphonyl-amino compounds. Suitable desulphonylating agents are above all alkali metal hydroxides or alkaline earth metal hydroxides, such as sodium hydroxide, potassium hydroxide and calcium hydroxide, alkali metal alkoxides, such as sodium methoxide, potassium methoxide, sodium ethoxide and potassium ethoxide, furthermore ammonia, alkylamines, such as methylamine, ethylamine, propylamine and butylamine, and also dialkylamines, such as dimethylamine and diethylamine. It is preferred to employ ammonia as the desulphonylating agent.

The desulphonylation is preferably carried out in the presence of diluents. Preferred diluents, besides water, are polar organic solvents, such as methanol, ethanol, propanol, isopropanol, 2-methoxyethanol, 2-ethoxyethanol and dioxane.

The desulphonylation is generally carried out at temperatures between 0° C. and 150° C., preferably at temperatures between 20° C. and 100° C.

In general, the reactants for desulphonylation are mixed at room temperature and stirred until the reaction is complete, if appropriate at increased temperature. For working up, the mixture is concentrated, if appropriate, diluted with water, and acidified using a strong acid, such as, for example, hydrochloric acid. The product, which is obtained in this process in the form of crystals (I, $R^2=H$), can be isolated by filtering off with suction.

If desired, salts can be prepared from the compounds of the general formula (I) according to the invention. Such salts are obtained in a simple manner by customary salt formation methods, for example by dissolving or dispersing a compound of the formula (I) in a suitable solvent, such as, for example, water, methanol, ethanol or acetone, and adding a suitable acid or base. The salts can then be isolated by concentration or filtering off with suction, if appropriate after stirring for some time.

Formula (IV) provides a general definition of the sulphonylaminotriazolinones to be used as starting substances in process (b) according to the invention for the preparation of compounds of the formula (I).

In formula (IV), $R^1$, $R^2$ and $R^3$ preferably, or in particular, have the meanings which have already been indicated above in connection with the description of the compounds of the formula (I) according to the invention as being preferred, or particularly preferred, for $R^1$, $R^2$ and $R^3$.

Starting substances of the formula (IV) which may be mentioned by way of example are:

4-(phenylsulphonylamino)-, 4-(2-chloro-phenylsulphonylamino)-4-(2-fluoro-phenylsulphonylamino)-, 4-(2-bromophenylsulphonylamino)-, 4-(2-methyl-phenylsulphonylamino)-, 4-(2-methoxy-phenylsulphonylamino)-, 4-(2-trifluoromethyl-phenylsulphonylamino)-, 4-(2-methylthio-phenylsulphonylamino)-, 4-(2-methylsulphonyl-phenylsulphonylamino)-, 4-(2-isopropoxycarbonyl-phenylsulphonylamino)-, 4-(2-chloro-6-methylphenylsulphonylamino)-, 4-(2-phenyl-phenylsulphonylamino)-, 4-(2-difluoromethoxy-phenylsulphonylamino)-, 4-(2-trifluoromethoxy-phenylsulphonylamino)-, 4-(2-dimethylaminosulphonyl-phenylsulphonylamino)-, 4-(2-methoxycarbonyl-phenylsulphonylamino)-, 4-(2-ethoxycarbonyl-phenylsulphonylamino)-, 4-(2-chlorophenylmethyl-sulphonylamino)-, 4-(2-methoxycarbonyl-phenylmethylsulphonylamino)-, 4-(2-ethoxycarbonyl-phenylmethylsulphonylamino)-, 4-(2-difluoromethoxy-phenylmethylsulphonylamino)-, 4-(2-trifluoromethoxy-phenylmethylsulphonylamino)-, 4-(1-methyl-4-methoxycarbonyl-pyrazol-5-yl-sulphonylamino)-, 4-(1-methyl-4-ethoxycarbonyl-pyrazol-5-yl-sulphonylamino)-, 4-(1-methyl-4-bromo-pyrazol-5-yl-sulphonylamino)-, 4-(2-methoxycarbonyl-thiophen-3-yl-sulphonylamino)-, 4-(3-trifluoromethyl-pyridin-2-yl-sulphonylamino)-, 4-(3-dimethylaminocarbonyl-pyridin-2-yl-sulphonylamino)-, and 4-(1-isoquinolinyl-4-ethoxycarbonyl-pyrazol-5-yl-sulphonylamino)- 2,4-dihydro-3H-1,2,4-triazol-3-one, -5-methyl-2,4-dihydro-3H-1,2,4-triazol-3-one, -5-ethyl-2,4-dihydro-3H-1,2,4-triazol-3-one, -5-propyl-2,4-dihydro-3H-1,2,4-triazol-3-one, -5-isopropyl-2,4-dihydro-3H-1,2,4-triazol-3-one, -5-trifluoromethyl-2,4-dihydro-3H-1,2,4-triazol-3-one, -5-methoxy-2,4-dihydro-3H-1,2,4-triazol-3-one, -5-methylthio-2,4-dihydro-3H-1,2,4-triazol-3-one, -5-t-butyl-2,4-dihydro-3H,1,2,4-triazol-3-one, -5-benzyl-2,4-dihydro-3H-1,2,4-triazol-3-one and -5-phenyl-2,4-dihydro-3H-1,2,4-triazol-3-one.

The sulphonylaminotriazolinones of the formula (IV) to be used as starting substances were hitherto unknown from the literature. The new compounds of the formula (IV) are obtained when aminotriazolinones of the general formula (VI)

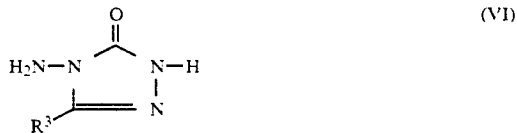

in which $R^3$ has the above-mentioned meaning, are reacted with sulphonyl halides or sulphonic anhydrides of the general formula (III)

in which $R^1$ and Q have the above-mentioned meanings, if appropriate, the presence of an acid acceptor, such as, for example, triethylamine, pyridine or 1,4-diazabicyclo-[2,2,2]-octane (DABCO), and, if appropriate, in the presence of a diluent, such as, for example, methylene chloride, tetrahydrofuran or dioxane, at temperatures between −50° C. and +50° C.

As far as the starting substances of the formulae (III) and (VI) are concerned, the instructions indicated above in the description of process (a) according to the invention, relating to these substances, are also true in this connection.

As far as the azines of the formula (V) are concerned, which are to be used as starting substances in process (b)

according to the invention, the instructions indicated above in the description of process (a) according to the invention are also true in this connection.

Process (b) according to the invention is preferably carried out using diluents. Suitable solvents are those which have been indicated above as diluents in process (a).

Process (b) is preferably carried out in the presence of an acid acceptor. Suitable acid acceptors are the same acid-binding agents which have been indicated above in process (a).

In process (b) according to the invention, the reaction temperatures can be varied within a relatively wide range. In general, the process is carried out at temperatures between 0° C. and +150° C., preferably at temperatures between +20° C. and +120° C.

Process (b) according to the invention is generally carried out under atmospheric pressure. However, it is also possible to carry out the process under increased or reduced pressure.

For carrying out process (b) according to the invention, the starting substances required in each case are generally employed in approximately equimolar amounts. However, it is also possible to use one of the two components employed in each case in a relatively large excess. The reactions are generally carried out in a suitable diluent in the presence of an acid acceptor, and the reaction mixture is stirred for several hours at the specific temperature required. Working-up in process (b) according to the invention is carried out in each case by customary methods.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucubita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are particularly suitable for selectively combating dicotyledon weeds in monocotyledon crops, above all using the post-emergence method.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beets, and 4-amino-6-(1,1-dimethylethyl)-3-methylthio-1,2,4-triazin-5(4H)-one (METRIBUZIN) for combating weeds in soy beans; 2,4-dichlorophenoxyacetic acid (2,4-D); 4-(2,4-dichlorophenoxy)-butyric acid (2,4-DB); 2,4-dichlorophenoxypropionic acid (2,4-DP); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxy-benzonitrile (BROMOXYNIL); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); 2-[4-(2,4-dichlorophenoxy)-phenoxy]-propionic acid, its methyl ester or its ethyl ester (DICLOFOP); 2-{4-[(6-chloro-2-benzoxazolyl)-oxy]-phenoxy}-propanoic acid, its methyl ester or its ethyl ester (FENOXAPROP); [(4-amino-3,5-dichloro-6-fluoro-2-pyridinyl)-oxy]-acetic acid or its 1-methyl-heptyl ester (FLUROXYPYR); methyl 2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)-urea (ISOPROTURON); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-{[[((4-methoxy-6-methyl-1,3,5-triazin-2-yl)-amino)-carbonyl]-amino]-sulphonyl}-benzoic acid or its methyl ester (METSULFURON); N-(1-ethylpropyl)-3,4-dimethyl-2,6-dinitroaniline (PENDIMETHALIN); O-(6-chloro-3-phenyl-pyridazin-4-yl) S-octyl thiocarbonate (PYRIDATE); 2-[1-(ethoxamino)-butylidene]-5-(2-ethylthiopropyl)-1,3-cyclohexadione (SETHOXYDIM); 4-ethylamino-2-t-butylamino-6-methylthio-s-triazine (TERBUTRYNE) and methyl 3-[[[[4-methoxy-6-methyl-1,3,5-triazin-2-yl)-amino]-carbonyl]-amino]-sulphonyl]-thiophene-2-carboxylate (THIAMETURON). Surprisingly, some mixtures also show synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

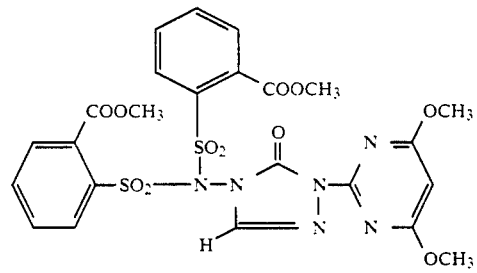

Process (a)

A mixture of 7.2 g (0.03 mol) of 4-amino-2-(4,6-dimethoxy-pyrimidin-2-yl)-2,4-dihydro-3H-1,2,4-triazol-3-one, 21.0 g (0.09 mol) of 2-methoxycarbonyl-benzenesulphonyl chloride and 50 ml of pyridine is stirred at 20° C. for 12 hours. The mixture is subsequently concentrated under a waterpump vacuum, and the residue is taken up in methylene chloride and washed with 2N hydrochloric acid. The mixture is dried using magnesium sulphate and then filtered, and the solvent is carefully distilled off from the filtrate under a waterpump vacuum.

12.0 g (63% of theory) of 4-[bis-(2-methoxycarbonyl-phenylsulphonyl)-amino]-2-(4,6-dimethoxy-pyrimidin-2-yl)-2,4-dihydro-3H-1,2,4-triazol-3-one are obtained as a crystalline residue of melting point 176° C.

Example 2

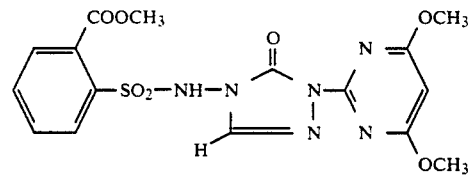

A mixture of 6.4 g (0.01 mol) of 4-[bis-(2-methoxycarbonyl-phenylsulphonyl)-amino]-2-(4,6-dimethoxy-pyrimidin-2-yl)-2,4-dihydro-3H-1,2,4-triazol-3-one (cf. Example 1), 100 ml of methanol and 10 ml of concentrated aqueous ammonia is stirred at 50° C. for 60 minutes. The mixture is subsequently concentrated under a waterpump vacuum, and the residue is taken up in water and acidified using 2N hydrochloric acid. The product which is obtained in this process in the form of crystals is isolated by filtering off with suction.

4.0 g (92% of theory) of 4-(2-methoxycarbonyl-phenylsulphonylamino)-2-(4,6-dimethoxy-pyrimidin-2-yl)-2,4-dihydro-3H-1,2,4-triazol-3-one of melting point 192° C. are obtained.

EXAMPLE 3

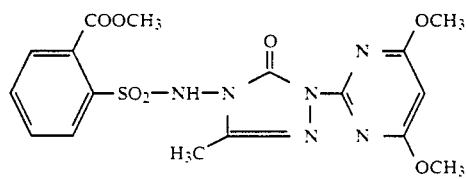

Process (a)

A mixture of 4.2 g (0.016 mol) of 4-amino-5-methyl-2-(4,6-dimethoxy-pyrimidin-2-yl)-2,4-dihydro-3H-1,2,4-triazol-3-one, 11.7 g (0.05 mol) of 2-methoxycarbonyl-benzenesulphonyl chloride and 50 ml of pyridine is stirred at 20° C. for 12 hours, then diluted with ice-water and acidified using 2N hydrochloric acid, and the mixture is shaken with methylene chloride. The organic phase is separated off, dried using magnesium sulphate and filtered. The solvent is carefully distilled off from the filtrate under a waterpump vacuum.

3.8 g (50% of theory) of 4-(2-methoxycarbonyl-phenylsulphonylamino)-5-methyl-2-(4,6-dimethoxy-pyrimidin-2-yl)-2,4-dihydro-3H-1,2,4-triazol-3-one are obtained as a crystalline residue of melting point 174° C.

EXAMPLE 4

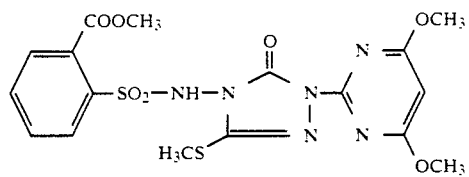

Process (a)

A mixture of 5.7 g (0.02 mol) of 4-amino-5-methylthio-2-(4,6-dimethoxy-pyrimidin-2-yl)-2,4-dihydro-3H-1,2,4-triazol-3-one, 14.0 g (0.06 mol) of 2-methoxycarbonyl-benzenesulphonyl chloride and 50 ml of pyridine is stirred at 20° C. for 48 hours. The mixture is subsequently concentrated under a waterpump vacuum, the residue is taken up in methylene chloride, and the mixture is washed using 2N hydrochloric acid, dried using magnesium sulphate and filtered. The filtrate is concentrated and the residue is purified by column chromatography on silica gel using methylene chloride/methanol (vol. 10:1).

3.0 g (31% of theory) of 4-(2-methoxycarbonyl-phenylsulphonylamino)-5-methylthio-2-(4,6-dimethoxy-pyrimidin-2-yl)-2,4-dihydro-3H-1,2,4-triazol-3-one of melting point 179° C. are obtained.

The compounds of the formula (I) which are listed in Table 2 below can be prepared analogously to Examples 1 to 4 and in accordance with the general description of the process according to the invention.

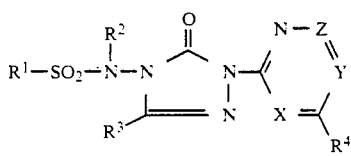

TABLE 2

Examples of the compounds of the formula (I)

| Example No. | R$^1$ | R$^2$ | R$^3$ | R$^4$ | X | Y | Z | Melting point (°C.) |
|---|---|---|---|---|---|---|---|---|
| 5 | ![COOC2H5-phenyl] COOC$_2$H$_5$ | H | H | SO$_2$CH$_3$ | N | CH | C—OCH$_3$ | 191 |
| 6 | ![COOC2H5-phenyl] COOC$_2$H$_5$ | H | CH$_3$ | SO$_2$CH$_3$ | N | CH | C—OCH$_3$ | 140 |
| 7 | ![COOCH3-phenyl-CH2] COOCH$_3$ —CH$_2$— | H | CH$_3$ | OCH$_3$ | N | CH | C—OCH$_3$ | 178 |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 8 | 2-(OCF₃)C₆H₄-CH₂- | H | CH₃ | OCH₃ | N | CH | C-OCH₃ | 186 |
| 9 | 2-(COOCH₃)C₆H₄- | 2-(COOCH₃)C₆H₄-SO₂- | H | CH₃ | N | CH | C-CH₃ | |
| 10 | 2-(COOCH₃)C₆H₄- | H | H | CH₃ | N | CH | C-CH₃ | |
| 11 | 2-(COOCH₃)C₆H₄- | Na | H | CH₃ | N | CH | C-CH₃ | |
| 12 | 2-(COOC₂H₅)C₆H₄- | 2-(COOC₂H₅)C₆H₄-SO₂- | H | CH₃ | N | CH | C-CH₃ | |
| 13 | 2-(COOC₂H₅)C₆H₄- | H | H | CH₃ | N | CH | C-CH₃ | |
| 14 | 2-F-C₆H₄- | 2-F-C₆H₄-SO₂- | H | CH₃ | N | CH | C-CH₃ | |
| 15 | 2-F-C₆H₄- | H | H | CH₃ | N | CH | C-CH₃ | |
| 16 | 2-Br-C₆H₄- | 2-Br-C₆H₄-SO₂- | H | CH₃ | N | CH | C-CH₃ | |
| 17 | 2-Br-C₆H₄- | H | H | CH₃ | N | CH | C-CH₃ | |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 18 | 2-CF₃-phenyl | 2-CF₃-phenyl-SO₂— | H | CH₃ | N | CH | C—CH₃ | |
| 19 | 2-CF₃-phenyl | H | H | CH₃ | N | CH | C—CH₃ | |
| 20 | 2-OCHF₂-phenyl | 2-OCHF₂-phenyl-SO₂— | H | CH₃ | N | CH | C—CH₃ | |
| 21 | 2-OCHF₂-phenyl | 2-OCHF₂-phenyl-SO₂— | H | CH₃ | N | N | C—CH₃ | |
| 22 | 2-OCHF₂-phenyl | H | H | CH₃ | N | CH | C—CH₃ | |
| 23 | 2-OCF₃-phenyl | 2-OCF₃-phenyl-SO₂— | H | CH₃ | N | CH | C—CH₃ | |
| 24 | 2-SO₂CH₃-phenyl | 2-SO₂CH₃-phenyl-SO₂— | H | CH₃ | N | CH | C—CH₃ | |
| 25 | 2-OCF₃-phenyl | H | H | CH₃ | N | CH | C—CH₃ | |
| 26 | 2-SO₂CH₃-phenyl | H | H | CH₃ | N | CH | C—CH₃ | |
| 27 | 2-SO₂N(CH₃)₂-phenyl | H | H | CH₃ | N | CH | C—CH₃ | |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 28 | 2-(SCH₃)-phenyl | H | H | CH₃ | N | CH | C—CH₃ | |
| 29 | 2-(OCH₃)-phenyl | H | H | CH₃ | N | CH | C—CH₃ | |
| 30 | 2-(COOCH₃)-phenyl | 2-(COOCH₃)-phenyl-SO₂— | H | CH₃ | N | CH | C—OCH₃ | |
| 31 | 2-(COOCH₃)-phenyl | H | H | CH₃ | N | CH | C—OCH₃ | |
| 32 | 2-(COOC₂H₅)-phenyl | 2-(COOC₂H₅)-phenyl-SO₂— | H | CH₃ | N | CH | C—OCH₃ | |
| 33 | 2-(COOC₂H₅)-phenyl | H | H | CH₃ | N | CH | C—OCH₃ | |
| 34 | 3-CH₃-2-(COOCH₃)-thienyl | 3-(SO₂—)-2-(COOCH₃)-thienyl | H | CH₃ | N | CH | C—OCH₃ | |
| 35 | 3-CH₃-2-(COOCH₃)-thienyl | H | H | CH₃ | N | CH | C—OCH₃ | |
| 36 | 2-Cl-phenyl | H | H | CH₃ | H | CH | C—OCH₃ | |
| 37 | 2-F-phenyl | H | H | CH₃ | H | CH | C—OCH₃ | |
| 38 | 2-Cl-phenyl | 2-Cl-phenyl-SO₂— | H | CH₃ | N | CH | C—OCH₃ | |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 39 | 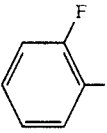 2-F-C₆H₄ | 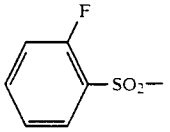 2-F-C₆H₄-SO₂— | H | CH₃ | N | CH | C—OCH₃ | |
| 40 | 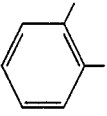 2-Br-C₆H₄ | 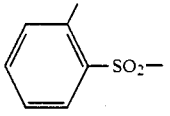 2-Br-C₆H₄-SO₂— | H | CH₃ | N | CH | C—OCH₃ | |
| 41 | 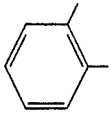 2-Br-C₆H₄ | H | H | CH₃ | N | CH | C—OCH₃ | |
| 42 | 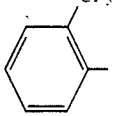 2-CF₃-C₆H₄ | 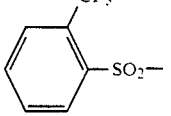 2-CF₃-C₆H₄-SO₂— | H | CH₃ | N | CH | C—OCH₃ | |
| 43 | 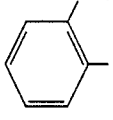 2-CF₃-C₆H₄ | H | H | CH₃ | N | CH₃ | C—OCH₃ | |
| 44 | 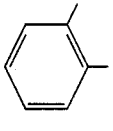 2-OCHF₂-C₆H₄ | 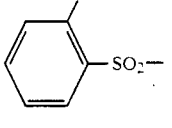 2-OCHF₂-C₆H₄-SO₂— | H | CH₃ | N | CH | C—OCH₃ | |
| 45 | 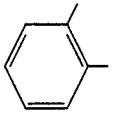 2-OCHF₂-C₆H₄ | H | H | CH₃ | N | CH | C—OCH₃ | |
| 46 | 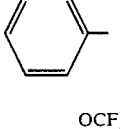 2-OCF₃-C₆H₄ | 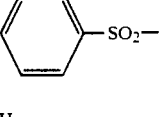 2-OCF₃-C₆H₄-SO₂— | H | CH₃ | N | CH | C—OCH₃ | |
| 47 | 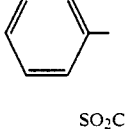 2-OCF₃-C₆H₄ | H | H | CH₃ | N | CH | C—OCH₃ | 219 |
| 48 | 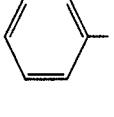 2-SO₂CH₃-C₆H₄ | H | H | CH₃ | N | CH | C—OCH₃ | |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 49 | 2-SO₂N(CH₃)₂-phenyl | H | H | CH₃ | N | CH | C—OCH₃ | |
| 50 | 2-SCH₃-phenyl | H | H | CH₃ | N | CH | C—OCH₃ | |
| 51 | 2-Cl-phenyl | 2-Cl-phenyl-SO₂— | H | CH₃ | N | CH | C—CH₃ | |
| 52 | 2-Cl-phenyl | H | H | CH₃ | N | CH | C—CH₃ | |
| 53 | 2-COOC₂H₅-phenyl | 2-COOC₂H₅-phenyl-SO₂— | H | OCH₃ | N | CH | C—OCH₃ | |
| 54 | 2-COOC₂H₅-phenyl | H | H | OCH₃ | N | CH | C—OCH₃ | |
| 55 | 3-methyl-2-COOCH₃-thienyl | 3-SO₂—-2-COOCH₃-thienyl | H | OCH₃ | N | CH | C—OCH₃ | |
| 56 | 3-methyl-2-COOCH₃-thienyl | H | H | OCH₃ | N | CH | C—OCH₃ | |
| 57 | 2-Cl-phenyl | 2-Cl-phenyl-SO₂— | H | OCH₃ | N | CH | C—OCH₃ | |
| 58 | 2-Cl-phenyl | H | H | OCH₃ | N | CH | C—OCH₃ | |
| 59 | 2-F-phenyl | 2-F-phenyl-SO₂— | H | OCH₃ | N | CH | C—OCH₃ | |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 60 | 2-F-phenyl | H | H | OCH₃ | N | CH | C—OCH₃ | |
| 61 | 2-Br-phenyl | 2-Br-phenyl-SO₂— | H | OCH₃ | N | CH | C—OCH₃ | |
| 62 | 2-Br-phenyl | H | H | OCH₃ | N | CH | C—OCH₃ | |
| 63 | 2-CF₃-phenyl | 2-CF₃-phenyl-SO₂— | H | OCH₃ | N | CH | C—OCH₃ | |
| 64 | 2-CF₃-phenyl | H | H | OCH₃ | N | CH | C—OCH₃ | |
| 65 | 2-OCHF₂-phenyl | 2-OCHF₂-phenyl-SO₂— | H | OCH₃ | N | CH | C—OCH₃ | |
| 66 | 2-OCHF₂-phenyl | H | H | OCH₃ | N | CH | C—OCH₃ | |
| 67 | 2-OCF₃-phenyl | 2-OCF₃-phenyl-SO₂— | H | OCH₃ | N | CH | C—OCH₃ | |
| 68 | 2-OCF₃-phenyl | H | H | OCH₃ | N | CH | C—OCH₃ | 208 |
| 69 | 2-SO₂CH₃-phenyl | H | H | OCH₃ | N | CH | C—OCH₃ | |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 70 | 2-(SCH₃)-C₆H₄– | H | H | OCH₃ | N | CH | C—OCH₃ | |
| 71 | 2-(SO₂N(CH₃)₂)-C₆H₄– | H | H | OCH₃ | N | CH | C—OCH₃ | |
| 72 | 2-(COOCH₃)-C₆H₄– | 2-(COOCH₃)-C₆H₄–SO₂– | H | CF₃ | N | CH | C—OCH₃ | |
| 73 | 2-(COOCH₃)-C₆H₄– | 2-(COOCH₃)-C₆H₄–SO₂– | H | OCH₃ | N | CH | C—Cl | |
| 74 | 2-(COOCH₃)-C₆H₄– | H | H | CF₃ | N | CH | C—OCH₃ | |
| 75 | 2-(COOC₂H₅)-C₆H₄– | 2-(COOC₂H₅)-C₆H₄–SO₂– | H | CF₃ | N | CH | C—OCH₃ | |
| 76 | 2-(COOC₂H₅)-C₆H₄– | H | H | CF₃ | N | CH | C—OCH₃ | |
| 77 | 2-(OCF₃)-C₆H₄– | H | H | CF₃ | N | CH | C—OCH₃ | |
| 78 | 2-(COOCH₃)-C₆H₄– | H | H | OCH₃ | N | CH | C—Cl | |
| 79 | 2-(COOC₂H₅)-C₆H₄– | 2-(COOC₂H₅)-C₆H₄–SO₂– | H | OCH₃ | N | CH | C—Cl | |

TABLE 2-continued

Examples of the compounds of the formula (I)

| Example No. | R¹ | R² | R³ | R⁴ | X | Y | Z |
|---|---|---|---|---|---|---|---|
| 80 | 2-(COOC₂H₅)-phenyl | H | H | OCH₃ | N | CH | C—Cl |
| 81 | 2-(OCHF₂)-phenyl | H | H | OCH₃ | N | CH | C—Cl |
| 82 | 2-(OCHF₂)-phenyl | 2-(OCHF₂)-phenyl-SO₂— | H | OCH₃ | N | CH | C—Cl |
| 83 | 2-(OCF₃)-phenyl | 2-(OCF₃)-phenyl-SO₂— | H | OCH₃ | N | CH | C—Cl |
| 84 | 2-(OCF₃)-phenyl | H | H | OCH₃ | N | CH | C—Cl |
| 85 | 2-(COOCH₃)-phenyl | 2-(COOCH₃)-phenyl-SO₂— | H | OCH₃ | N | CH | C—OCHF₂ |
| 86 | 2-(COOCH₃)-phenyl | H | H | OCH₃ | N | CH | C—OCHF₂ |
| 87 | 2-(COOC₂H₅)-phenyl | 2-(COOC₂H₅)-phenyl-SO₂— | H | OCH₃ | N | CH | C—OCHF₂ |
| 88 | 2-(COOC₂H₅)-phenyl | H | H | OCH₃ | N | CH | C—OCHF₂ |
| 89 | 3-(COOCH₃)-thien-2-yl | 3-(SO₂—)-thien-2-yl-COOCH₃ | H | OCH₃ | N | CH | C—OCHF₂ |
| 90 | 3-(COOCH₃)-thien-2-yl | H | H | OCH₃ | N | CH | C—OCHF₂ |

TABLE 2-continued

Examples of the compounds of the formula (1)

| Example No. | R¹ | R² | R³ | R⁴ | X | Y | Z | Melting point (°C.) |
|---|---|---|---|---|---|---|---|---|
| 91 | 2-(COOCH₃)-phenyl | 2-(COOCH₃)-phenyl-SO₂— | H | OCHF₂ | N | CH | C—OCHF₂ | 198 |
| 92 | 2-(COOCH₃)-phenyl | H | H | OCHF₂ | N | CH | C—OCHF₂ | 180 |
| 93 | 2-(COOC₂H₅)-phenyl | 2-(COOC₂H₅)-phenyl-SO₂— | H | OCHF₂ | N | CH | C—OCHF₂ | |
| 94 | 2-(COOC₂H₅)-phenyl | H | H | OCHF₂ | N | CH | C—OCHF₂ | |
| 95 | 3-methyl-2-(COOCH₃)-thienyl | 3-(SO₂—)-2-(COOCH₃)-thienyl | H | OCHF₂ | N | CH | C—OCHF₂ | |
| 96 | 3-methyl-2-(COOCH₃)-thienyl | H | H | OCHF₂ | N | CH | C—OCHF₂ | |
| 97 | 2-Cl-phenyl | 2-Cl-phenyl-SO₂— | H | OCHF₂ | N | CH | C—OCHF₂ | |
| 98 | 2-Cl-phenyl | H | H | OCHF₂ | N | CH | C—OCHF₂ | |
| 99 | 2-(COOCH₃)-benzyl (—CH₂—) | 2-(COOCH₃)-benzyl-CH₂—SO₂— | H | OCH₃ | N | CH | C—OCH₃ | |
| 100 | 2-(COOC₂H₅)-benzyl (—CH₂—) | H | H | OCH₃ | N | CH | C—OCH₃ | |
| 101 | 2-(COOCH₃)-benzyl (—CH₂—) | 2-(COOCH₃)-benzyl-CH₂—SO₂— | H | OCH₃ | N | CH | C—Cl | |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 102 | 2-(COOCH₃)-benzyl- (C₆H₄(COOCH₃)-CH₂-) | H | H | OCH₃ | N | CH | C—Cl | |
| 103 | 2-(COOC₂H₅)-benzyl- | 2-(COOC₂H₅)-C₆H₄-CH₂-SO₂- | H | OCH₃ | N | CH | C—OCH₃ | |
| 104 | 2-(COOC₂H₅)-benzyl- | H | H | OCH₃ | N | CH | C—OCH₃ | |
| 105 | 2-Cl-benzyl- | 2-Cl-C₆H₄-CH₂-SO₂- | H | OCH₃ | N | CH | C—OCH₃ | |
| 106 | 2-Cl-benzyl- | H | H | OCH₃ | N | CH | C—OCH₃ | |
| 107 | 2-Br-benzyl- | 2-Br-C₆H₄-CH₂-SO₂- | H | OCH₃ | N | CH | C—OCH₃ | |
| 108 | 2-Br-benzyl- | 2-Br-C₆H₄-CH₂-SO₂- | H | OCH₃ | N | CH | C—OCHF₂ | |
| 109 | 2-Br-benzyl- | H | H | OCH₃ | N | CH | C—OCH₃ | |
| 110 | 2-(COOCH₃)-benzyl- | 2-(COOCH₃)-C₆H₄-CH₂-SO₂- | H | OCH₃ | N | CH | C—OCHF₂ | |
| 111 | 2-(COOC₂H₅)-benzyl- | H | H | CH₃ | N | N | C—CH₃ | |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 112 | 3-methyl-2-(methoxycarbonyl)thiophen-yl | 3-(methoxycarbonyl)thiophen-2-ylsulfonyl (SO₂–) | H | CH₃ | N | N | C–CH₃ | |
| 113 | 2-chlorophenyl | 2-chlorophenylsulfonyl (SO₂–) | H | CH₃ | N | N | C–CH₃ | |
| 114 | 2-(methoxycarbonyl)phenyl | 2-(methoxycarbonyl)phenylsulfonyl (SO₂–) | H | CH₃ | N | N | C–OCH₃ | |
| 115 | 2-(methoxycarbonyl)phenyl | H | H | CH₃ | N | N | C–OCH₃ | |
| 116 | 2-(ethoxycarbonyl)phenyl | 2-(ethoxycarbonyl)phenylsulfonyl (SO₂–) | H | CH₃ | N | N | C–OCH₃ | |
| 117 | 2-(ethoxycarbonyl)phenyl | H | H | CH₃ | N | N | C–OCH₃ | |
| 118 | 3-methyl-2-(methoxycarbonyl)thiophen-yl | 3-(methoxycarbonyl)thiophen-2-ylsulfonyl (SO₂–) | H | CH₃ | N | N | C–OCH₃ | |
| 119 | 2-(methoxycarbonyl)thiophen-3-yl | H | H | CH₃ | N | N | C–OCH₃ | |
| 120 | 2-chlorophenyl | Na | H | CH₃ | N | N | C–OCH₃ | |
| 121 | 2-chlorophenyl | 2-chlorophenylsulfonyl (SO₂–) | H | CH₃ | N | N | C–OCH₃ | |
| 122 | 2-chlorophenyl | H | H | CH₃ | N | N | C–OCH₃ | |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 123 | 2-COOCH₃-phenyl | 2-COOCH₃-6-(SO₂−)-phenyl | H | OCH₃ | N | N | C—OCH₃ | |
| 124 | 2-COOCH₃-phenyl | H | H | OCH₃ | N | N | C—OCH₃ | |
| 125 | 2-COOC₂H₅-phenyl | 2-COOC₂H₅-6-(SO₂−)-phenyl | H | OCH₃ | N | N | C—OCH₃ | |
| 126 | 2-COOC₂H₅-phenyl | H | H | OCH₃ | N | N | C—OCH₃ | |
| 127 | 3-methyl-2-COOCH₃-thienyl | 3-(SO₂−)-2-COOCH₃-thienyl | H | OCH₃ | N | N | C—OCH₃ | |
| 128 | 3-methyl-2-COOCH₃-thienyl | H | H | OCH₃ | N | N | C—OCH₃ | |
| 129 | 2-Cl-phenyl | 2-Cl-6-(SO₂−)-phenyl | H | OCH₃ | N | N | C—OCH₃ | |
| 130 | 2-Cl-phenyl | H | H | OCH₃ | N | N | C—OCH₃ | |
| 131 | 2-F-phenyl | 2-F-6-(SO₂−)-phenyl | H | OCH₃ | N | N | C—OCH₃ | |
| 132 | 2-F-phenyl | H | H | OCH₃ | N | N | C—OCH₃ | |
| 133 | 2-Br-phenyl | 2-Br-6-(SO₂−)-phenyl | H | OCH₃ | N | N | C—OCH₃ | |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 134 | 2-Br-C₆H₄- | H | H | OCH₃ | N | N | C—OCH₃ | |
| 135 | 2-CF₃-C₆H₄- | 2-CF₃-C₆H₄-SO₂- | H | OCH₃ | N | N | C—OCH₃ | |
| 136 | 2-CF₃-C₆H₄- | H | H | OCH₃ | N | N | C—OCH₃ | |
| 137 | 2-OCHF₂-C₆H₄- | 2-OCHF₂-C₆H₄-SO₂- | H | OCH₃ | N | N | C—OCH₃ | |
| 138 | 2-OCHF₂-C₆H₄- | H | H | OCH₃ | N | N | C—OCH₃ | |
| 139 | 2-OCF₃-C₆H₄- | 2-OCF₃-C₆H₄-SO₂- | H | OCH₃ | N | N | C—OCH₃ | |
| 140 | 2-OCF₃-C₆H₄- | H | H | OCH₃ | N | N | C—OCH₃ | 201 |
| 141 | 2-COOCH₃-C₆H₄-CH₂- | 2-COOCH₃-C₆H₄-CH₂-SO₂- | H | OCHF₂ | N | CH | C—OCHF₂ | |
| 142 | 2-OCHF₂-C₆H₄-CH₂- | 2-OCHF₂-C₆H₄-CH₂-SO₂- | H | OCH₃ | N | CH | C—OCH₃ | |
| 143 | 2-OCF₃-C₆H₄-CH₂- | 2-OCF₃-C₆H₄-CH₂-SO₂- | H | OCH₃ | N | CH | C—OCH₃ | |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 144 | 2-(COOCH₃)-phenyl- | 2-(COOCH₃)-phenyl-SO₂- | H | CH₃ | N | N | C—CH₃ | |
| 145 | 2-(COOCH₃)-phenyl- | H | H | CH₃ | N | N | C—CH₃ | |
| 146 | 2-(COOC₂H₅)-phenyl- | 2-(COOC₂H₅)-phenyl-SO₂- | H | CH₃ | N | N | C—CH₃ | |
| 147 | 2-(SCH₃)-phenyl- | 2-(SCH₃)-phenyl-SO₂- | H | OCH₃ | N | N | C—OCH₃ | |
| 148 | 2-(SO₂CH₃)-phenyl- | 2-(SO₂CH₃)-phenyl-SO₂- | H | OCH₃ | N | N | C—OCH₃ | |
| 149 | 2-(SO₂N(CH₃)₂)-phenyl- | 2-(SO₂N(CH₃)₂)-phenyl-SO₂- | H | OCH₃ | N | N | C—OCH₃ | |
| 150 | 2-(COOCH₃)-phenyl- | 2-(COOCH₃)-phenyl-SO₂- | H | OCH₃ | N | N | C—Cl | |
| 151 | 2-(COOCH₃)-phenyl- | 2-(COOCH₃)-phenyl-SO₂- | H | C₂H₅ | N | N | C—OCH₃ | |
| 152 | 2-(COOCH₃)-phenyl-CH₂- | 2-(COOCH₃)-phenyl-CH₂-SO₂- | H | OCH₃ | N | N | C—OCH₃ | |
| 153 | 2-(COOCH₃)-phenyl-CH₂- | H | H | OCH₃ | N | N | C—OCH₃ | |

TABLE 2-continued
Examples of the compounds of the formula (1)
| Example No. | R¹ | R² | R³ | R⁴ | X | Y | Z | Melting point (°C.) |
|---|---|---|---|---|---|---|---|---|
| 154 | 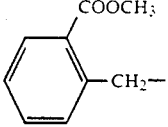 | H | H | OCH₃ | N | N | C—CH₃ | |
| 155 | 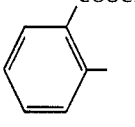 | 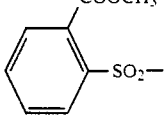 | H | OCH₃ | N | N | C—NHC₂H₅ | |
| 156 | 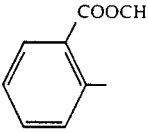 | 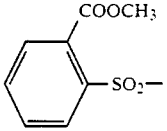 | H | OC₂H₅ | N | N | C—NHCH₃ | |
| 157 | 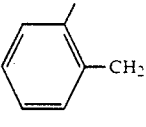 | 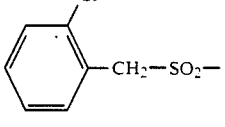 | H | OCH₃ | N | N | C—OCH₃ | |
| 158 | 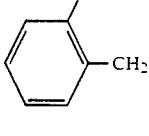 | 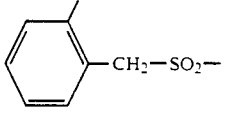 | H | OCH₃ | N | N | C—OCH₃ | |
| 159 | 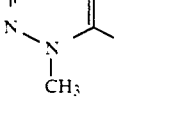 | 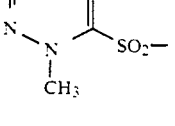 | H | OCH₃ | N | CH | C—OCH₃ | |
| 160 | 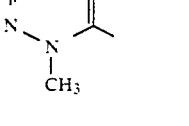 | H | H | OCH₃ | N | CH | C—OCH₃ | |
| 161 | 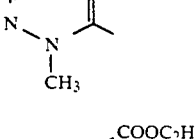 | 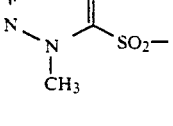 | H | OCH₃ | N | CH | C—OCH₃ | |
| 162 | 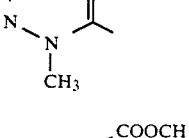 | H | H | OCH₃ | N | CH | C—OCH₃ | |
| 163 | 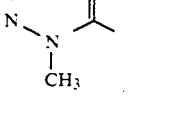 | 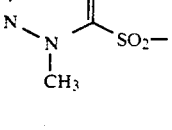 | H | OCH₃ | N | N | C—OCH₃ | |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 164 | 3-(COOCH₃)-1-methyl-pyrazol-5-yl | H | H | OCH₃ | N | N | C—OCH₃ | |
| 165 | 3-(COOC₂H₅)-1-methyl-pyrazol-5-yl | 3-(COOC₂H₅)-1-methyl-pyrazol-4-yl-SO₂— | H | OCH₃ | N | N | C—OCH₃ | |
| 166 | 3-(COOC₂H₅)-1-methyl-pyrazol-5-yl | H | H | OCH₃ | N | N | C—OCH₃ | |
| 167 | 3-chloro-4-methyl-isothiazol-5-yl | 3-chloro-isothiazol-4-yl-SO₂— | H | OCH₃ | N | N | C—OCH₃ | |
| 168 | 3-chloro-4-methyl-isothiazol-5-yl | 3-chloro-isothiazol-4-yl-SO₂— | H | CH₃ | N | CH | C—CH₃ | |
| 169 | 3-chloro-4-methyl-isothiazol-5-yl | H | H | CH₃ | N | CH | C—CH₃ | |
| 170 | 4-chloro-3-(COOCH(CH₃)₂)-phenyl | H | H | OCH₃ | N | N | C—OCH₃ | |
| 171 | 4-(OCHF₂)-3-(COOC₂H₅)-phenyl | H | H | OCH₃ | N | CH | C—OCH₃ | |
| 172 | 3-(CF₃)-pyridin-2-yl | H | H | OCH₃ | N | CH | C—OCH₃ | |
| 173 | 2-(C₆H₅)-phenyl | H | H | OCH₃ | N | CH | C—OCH₃ | |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 174 | 2-($C_6H_5$)-phenyl | H | H | $OCH_3$ | N | N | $C-OCH_3$ | |
| 175 | 2-($CH_3$)-phenyl | H | H | $OCH_3$ | N | N | $C-OCH_3$ | |
| 176 | 2-($SC_3H_7$)-phenyl | H | H | $OCH_3$ | N | N | $C-OCH_3$ | |
| 177 | 2-[$SO_2-N(CH_3)(OCH_3)$]-phenyl | H | H | $OCH_3$ | N | H | $C-OCH_3$ | |
| 178 | 2-($OC_6H_5$)-phenyl | H | H | $OCH_3$ | N | N | $C-OCH_3$ | |
| 179 | 2-($COOCH_3$)-phenyl | H | $CH_3$ | $CH_3$ | N | CH | $C-CH_3$ | 233 |
| 180 | 2-($COOCH_3$)-thien-3-yl | H | $CH_3$ | $CH_3$ | N | CH | $C-CH_3$ | |
| 181 | 2-($COOCH_3$)-phenyl | H | $SCH_3$ | $CH_3$ | N | CH | $C-CH_3$ | |
| 182 | 2-($COOC_2H_5$)-phenyl | H | $CH_3$ | $CH_3$ | N | CH | $C-CH_3$ | |
| 183 | 2-($COOCH_3$)-benzyl | H | $SCH_3$ | $OCH_3$ | N | CH | $C-OCH_3$ | |
| 184 | 2-($COOCH_3$)-thien-3-yl | H | $CH_3$ | $OCH_3$ | N | N | $C-OCH_3$ | |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 185 | 2-Cl-C₆H₄ | H | CH₃ | CH₃ | N | N | C—OCH₃ | |
| 186 | 2-COOCH₃-C₆H₄ | H | CH₃ | CH₃ | N | N | C—OCH₃ | |
| 187 | 2-COOCH₃-C₆H₄ | H | CH₃ | OCH₃ | N | N | C—OCH₃ | 202 |
| 188 | 2-COOC₂H₅-C₆H₄ | H | CH₃ | OCH₃ | N | CH | C—Cl | |
| 189 | 2-C₆H₅-C₆H₄ | H | CH₃ | OCH₃ | N | CH | C—OCH₃ | |
| 190 | 2-C₆H₅-C₆H₄ | H | CH₃ | OCH₃ | N | N | C—OCH₃ | |
| 191 | 3-methyl-2-COOCH₃-thienyl | H | CH₃ | CH₃ | N | N | C—OCH₃ | |
| 192 | 3-methyl-2-COOCH₃-thienyl | 3-SO₂-2-COOCH₃-thienyl | H | CH₃ | N | CH | C—CH₃ | |
| 193 | 3-methyl-2-COOCH₃-thienyl | H | H | CH₃ | N | CH | C—CH₃ | |
| 194 | 2-Cl-C₆H₄ | H | SCH₃ | CH₃ | N | N | C—OCH₃ | |
| 195 | 2-COOCH₃-C₆H₄ | H | SCH₃ | CH₃ | N | N | C—OCH₃ | |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 196 | 2-(COOCH₃)-phenyl | H | SCH₃ | OCH₃ | N | N | C—OCH₃ | |
| 197 | 2-(COOC₂H₅)-phenyl | H | H | SO₂CH₃ | CH | N | C—OCH₃ | |
| 198 | 2-(COOC₂H₅)-phenyl | H | CH₃ | SO₂CH₃ | CH | N | C—OCH₃ | |
| 199 | 2-(COOCH₃)-phenyl | 2-(COOCH₃)-phenyl-SO₂— | CH₃ | OCHF₂ | CH | N | C—OCHF₂ | 200 |
| 200 | 2-(COOCH₃)-phenyl | 2-(COOCH₃)-phenyl-SO₂— | C₂H₅ | CH₃ | N | N | C—OCH₃ | |
| 201 | 2-(COOCH₃)-benzyl | H | CH(CH₃)₂ | OCH₃ | N | CH | C—OCH₃ | |
| 202 | 2-(COOCH₃)-phenyl | H | CH₂CH(CH₃)₂ | OCH₃ | N | N | C—OCH₃ | |
| 203 | 2-(OCF₃)-phenyl | H | C(CH₃)₃ | CH₃ | N | CH | C—OCH₃ | |
| 204 | 2-(COOCH₃)-benzyl | H | C(CH₃)₃ | OCH₃ | N | CH | C—OCH₃ | |
| 205 | 2-(COOCH₃)-phenyl | H | CF₃ | CH₃ | N | N | C—OCH₃ | |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 206 | 2-(COOCH₃)-phenyl | H | CH₃ | OCHF₂ | N | CH | C—OCHF₂ | 118 |
| 207 | 1-methyl-5-methyl-4-(COOC₂H₅)-pyrazol-3-yl | H | CH₃ | OCH₃ | N | CH | C—OCH₃ | 198 |
| 208 | 2-(COOCH₃)-phenyl | H | C₂H₅ | OCH₃ | N | CH | C—OCH₃ | 174 |
| 209 | 2-Cl-phenyl | 2-Cl-phenyl-SO₂— | CH₃ | OCH₃ | N | CH | C—OCH₃ | 204 |
| 210 | 2-(COOCH₃)-phenyl | H | C₃H₇ | OCH₃ | N | CH | C—OCH₃ | 179 |
| 211 | 2-(COOCH₃)-phenyl | 2-(COOCH₃)-phenyl-SO₂— | CH(CH₃)₂ | OCH₃ | N | CH | C—OCH₃ | 184 |
| 212 | 2-(COOCH₃)-phenyl | 2-(COOCH₃)-phenyl-SO₂— | CH₃ | CH₃ | N | CH | C—OCH₃ | |
| 213 | 2-(OCF₃)-phenyl | 2-(OCF₃)-phenyl-SO₂— | CH₃ | CH₃ | N | CH | C—OCH₃ | |
| 214 | 2-F-pyridyl | 2-F-phenyl-SO₂— | CH₃ | CH₃ | N | CH | C—OCH₃ | |
| 215 | 2,6-diCl-phenyl | 2,6-diCl-phenyl-SO₂— | CH₃ | CH₃ | N | CH | C—OCH₃ | |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 216 | 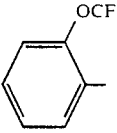 2-OCF₃-phenyl | H | CH₃ | CH₃ | N | CH | C—OCH₃ | |
| 217 | 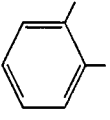 2-F-phenyl | H | CH₃ | CH₃ | N | CH | C—OCH₃ | 232 |
| 218 | 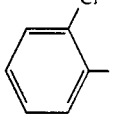 2-Cl-phenyl | H | CH₃ | CH₃ | N | CH | C—OCH₃ | 247 |
| 219 | 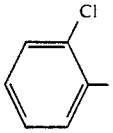 2-Cl-phenyl | 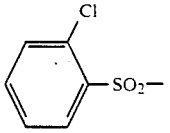 2-Cl-phenyl-SO₂— | CH₃ | CH₃ | N | CH | C—OCH₃ | 203 |
| 220 | 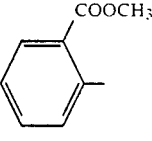 2-COOCH₃-phenyl | H | CH₃ | CH₃ | N | CH | C—OCH₃ | |
| 221 | 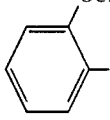 2-OCF₃-phenyl | H | CH₃ | CH₃ | N | CH | C—OCH₃ | 248 |
| 222 | 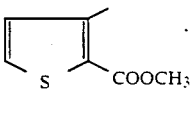 | 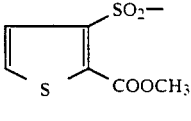 | CH₃ | CH₃ | N | CH | C—CH₃ | 206 |
| 223 | 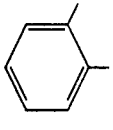 2-OCF₃-phenyl | H | CH₃ | CH₃ | N | CH | C—CH₃ | 308 |
| 224 | 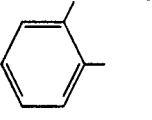 2-COOCH₃-phenyl | 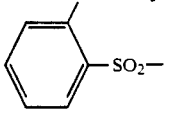 2-COOCH₃-phenyl-SO₂— | CH₃ | CH₃ | N | CH | C—CH₃ | 195 |
| 225 | 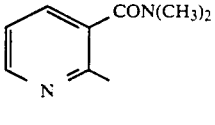 | H | H | OCH₃ | N | CH | C—OCH₃ | |
| 226 | 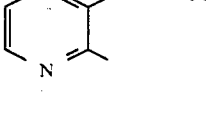 | H | CH₃ | OCH₃ | N | CH | C—OCH₃ | |

TABLE 2-continued

Examples of the compounds of the formula (I)

| Example No. | R¹ | R² | R³ | R⁴ | X | Y | Z | Melting point (°C.) |
|---|---|---|---|---|---|---|---|---|
| 227 | 6-methyl-2-methyl-3-(N,N-dimethylcarbamoyl)pyridin-yl | H | $CH_3$ | $OCH_3$ | N | CH | C—$OCH_3$ | |
| 228 | 5-chloro-3-methoxycarbonyl-1-methylpyrazol-4-yl | H | $SCH_3$ | $OCH_3$ | N | CH | C—$OCH_3$ | |
| 229 | 2-(trifluoromethoxy)phenyl | H | $CH_3$ | $OCH_3$ | N | N | C—$OCH_3$ | 179 |
| 230 | 2-chlorophenyl | H | $CH_3$ | $OCH_3$ | N | N | C—$OCH_3$ | (amorphous) |
| 231 | 2-fluorophenyl | H | $CH_3$ | $OCH_3$ | N | N | C—$OCH_3$ | 87 |

The preparation in accordance with process (b) of the compound listed as Example No. 221 in Table 2 is described below by way of example:

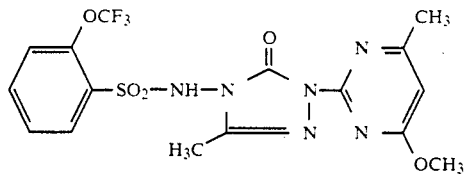

Process (b)

A mixture of 23.1 g (0.070 mol) of 4-(2-trifluoromethoxy-phenylsulphonylamino)-5-methyl-2,4-dihydro-3H-1,2,4-triazol-3-one, 14.5 g (0.072 mol) of 4-methoxy-6-methyl-2-methylsulphonyl-pyrimidine, 50 g of potassium carbonate and 300 ml dioxane is refluxed for 6 hours. The mixture is allowed to cool and then filtered, the filter residue is washed with water and then taken up in methylene chloride and 5% strength hydrochloric acid, and the mixture is shaken. The organic phase is dried using sodium sulphate and filtered. After the filtrate has been concentrated, the residue is made to crystallize by trituration with ethanol, and the crystalline product is isolated by filtering off with suction.

6.0 g (21% of theory) of 4-(2-trifluoromethoxy-phenylsulphonylamino)-5-methyl-2-(4-methoxy-6-methylpyrimidin-2-yl)-2,4-dihydro-3H-1,2,4-triazol-3-one of melting point 248° C. are obtained.

STARTING SUBSTANCES OF THE FORMULA (II)

Example (II-1)

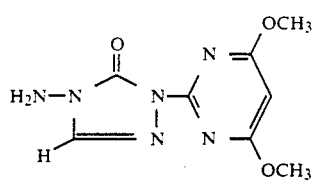

A mixture of 7.0 g (0.05 mol) of 4-(1-methyl-ethylideneamino)-2,4-dihydro-3H-1,2,4-triazol-3-one, 21 g (0.15 mol) of potassium carbonate, 11.0 g (0.05 mol) of 4,6-dimethoxy-2-methylsulphonyl-pyrimidine and 100 ml of acetonitrile is refluxed for 3 hours. After the mixture has cooled, it is filtered and the filtrate is concentrated, the residue is taken up in 100 ml of ethanol/water (vol. 1:1), and the mixture is stirred for 3 hours at 60° C. after 1 ml of concentrated hydrochloric acid has been added. The mixture is concentrated, the residue is then triturated with ethanol, and the product obtained in the form of crystals is isolated by filtering off with suction.

9.7 g (82% of theory) of 4-amino-2-(4,6-dimethoxy-pyrimidin-2-yl)-2,4-dihydro-3H-1,2,4-triazol-3-one of melting point 238° C. are obtained.

Example (II-2)

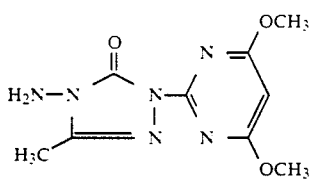

A mixture of 4.0 g (0.02 mol) of 4-(1,3-dimethyl-butylideneamino)-5-methyl-2,4-dihydro-3H-1,2,4-triazol-3-one, 8.3 g (0.06 mol) of potassium carbonate, 4.4 g (0.02 mol) of 4,6-dimethoxy-2-methylsulphonyl-pyrimidine and 100 ml of acetonitrile is refluxed for 3 hours. After the mixture has cooled it is filtered, the filtrate is concentrated, the residue is taken up in 100 ml of ethanol/water (vol. 1:1) and stirred for 60 minutes at 60° C. after 2 drops of concentrated hydrochloric acid have been added. The mixture is concentrated, the residue is stirred with saturated sodium hydrogen carbonate solution, and the crystalline product is isolated by filtering off with suction.

2.6 g (52% of theory) of 4-amino-5-methyl-2-(4,6-dimethoxy-pyrimidin-2-yl)-2,4-dihydro-3H-1,2,4-triazol-3-one of melting point 219° C. are obtained.

Example (II-3)

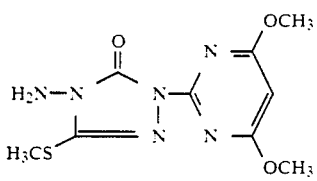

A mixture of 3.0 g (0.02 mol) of 4-amino-5-methylthio-2,4-dihydro-3H-1,2,4-triazol-3-one and 200 ml of acetone is refluxed for 4 hours after 0.1 g of p-toluenesulphonic acid has been added. The mixture is concentrated, the residue is taken up in 100 ml of acetonitrile, and the reaction mixture is refluxed for 12 hours after 8.3 g (0.06 mol) of potassium carbonate and 4.4 g (0.02 mol) of 4,6-dimethoxy-2-methylsulphonyl-pyrimidine have been added. The cooled mixture is filtered, the filtrate is concentrated, the residue is taken up in 100 ml of ethanol/water (vol. 1:1) and stirred for 3 hours at 60° C. after 2 ml of concentrated hydrochloric acid have been added. The mixture is concentrated, the residue is stirred with saturated sodium hydrogen carbonate solution, and the crystalline product is isolated by filtering off with suction.

4.9 g (86% of theory) of 4-amino-5-methylthio-2-(4,6-dimethoxy-pyrimidin-2-yl)-2,4-dihydro-3H-1,2,4-triazol-3-one of melting point 198° C. are obtained.

Example (II-4)

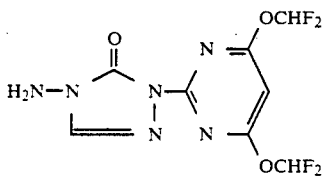

A mixture of 3.0 g (0.03 mol) of 4-amino-2,4-dihydro-3H-1,2,4-triazol-3-one, 8.7 g (0.03 mol) of 2-methanesulphonyl-4,6-bis-difluoromethoxy-pyrimidine and 12.4 g (0.09 mol) of potassium carbonate in 100 ml of dioxane is heated at 60° C. for approximately 4 hours with stirring. The mixture is concentrated in vacuo, the residue is stirred with water, and the insoluble precipitate is filtered off with suction and washed to neutrality using highly dilute hydrochloric acid and water. After drying, 7.0 g (0.0226 mol = 75% of theory) of 4-amino-2-(4,6-bis-difluoromethoxy)-pyrimidin-2-yl-2,4-dihydro-3H-1,2,4-triazol-3-one of melting point 195° C. remain.

The compounds of the formula (II) which are listed in Table 3 below can be prepared analogously to Examples (II-1) to (II-4).

TABLE 3

Preparation examples of the starting substances of the formula (II)

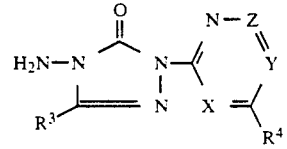

(II)

| Ex. No. | $R^3$ | $R^4$ | X | Y | Z | Melting point (°C.) |
|---|---|---|---|---|---|---|
| II-5 | $C(CH_3)_3$ | $OCH_3$ | N | CH | $C-OCH_3$ | 205 |
| II-6 | $CF_3$ | $OCH_3$ | N | CH | $C-OCH_3$ | 213 |
| II-7 | $C_2H_5$ | $OCH_3$ | N | CH | $C-OCH_3$ | 167 |
| II-8 | $C_3H_7$ | $OCH_3$ | N | CH | $C-OCH_3$ | 183 |
| II-9 | $CH(CH_3)_2$ | $OCH_3$ | N | CH | $C-OCH_3$ | 206 |
| II-10 | $CH_3$ | $CH_3$ | N | CH | $C-CH_3$ | 310 |
| II-11 | H | $OCH_3$ | N | CH | $C-NH-CH_3$ | |
| II-12 | H | $OCH_3$ | N | N | $C-OCH_3$ | |
| II-13 | $CH_3$ | $OCH_3$ | N | N | $C-CH_3$ | |
| II-14 | $CH_3$ | Cl | N | CH | $C-OCH_3$ | |
| II-15 | $PhCH_2-$ | $OCH_3$ | N | CH | $C-OCH_3$ | |
| II-16 | Ph-CH< | $OCH_3$ | N | CH | $C-OCH_3$ | |
| II-17 | $CH_3$ | $OCHF_2$ | N | CH | $C-OCHF_2$ | 255 |

STARTING SUBSTANCES OF THE FORMULA (IV)

Example (IV-1)

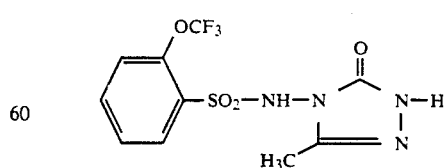

10.0 g (0.088 mol) of 4-amino-5-methyl-2,4-dihydro-3H-1,2,4-triazol-3-one are dissolved in 50 ml of dry pyridine, the mixture is cooled to −10° C., and 32.7 g (0.12 mol) of 2-trifluoromethoxy-benzenesulphonyl chloride are added. The reaction mixture is allowed to reach room temperature (approximately 20° C.) and stirred for approximately 12 hours. After the mixture has been concentrated, the residue is taken up in methylene chloride and shaken with 1N hydrochloric acid and then with water. The organic phase is dried with sodium sulfate and filtered. The solvent is carefully distilled off from the filtrate under a water pump vacuum. 23.1 g (80% of theory) of 4-(2-trifluoromethoxy-phenylsulphonylamino)-5-methyl-2,4-dihydro-3H-1,2,4-triazol-3-one are obtained as an oily residue.

$^1$H-NMR*): (DMSO, δ, ppm): 2.10 (s, CH$_3$), 7.55, 7.83, 7.93 (m, 4H), approximately 11.5 (m, 2×NH).

*) The $^1$H-NMR Spectra were recorded in dimethyl sulphoxide (DMSO) using tetramethylsilane (TMS) as the internal standard. The chemical shift is indicated as the −value in ppm.

The compounds of the formula (IV), which are listed in Table 4 below, can be prepared analogously.

A mixture of 4.0 g (0.04 mol) of 5-methyl-1,3,4-oxadiazol-2(3H)-one, 8.8 g (0.047 mol) of 4,6-dimethoxy-2-methylsulphonyl-pyrimidine, 16.9 g (0.12 mol) of potassium carbonate and 100 ml of acetonitrile is stirred for 4 hours at 60° C. The cold mixture is concentrated under a water-pump vacuum, the residue is stirred with water, and the crystalline product is isolated by filtering off with suction.

4.8 g (50% of theory) of 3-(4,6-dimethoxypyrimidin-2-yl)-5-methyl-1,3,4-oxadiazol-2(3H)-one of melting point 158° C. are obtained.

USE EXAMPLES

In the following Use Examples, the compound listed below is used as comparison substance:

TABLE 4

Preparation Examples of the starting substances of the formula (IV)

$$R^1-SO_2-N(R^2)-N-\overset{O}{\underset{R^3}{C}}-N(H)-N$$ (IV)

| Example No. | R$^1$ | R$^2$ | R$^3$ | Physical data |
|---|---|---|---|---|
| IV-2 | 2-COOCH$_3$-phenyl | H | CH$_3$ | NMR: 2.04$^{a)}$ |
| IV-3 | 2-Cl-phenyl | H | CH$_3$ | NMR: 2.04$^{a)}$ |
| IV-4 | 2-F-phenyl | H | CH$_3$ | NMR: 2.11$^{a)}$ |
| IV-5 | 4-CH$_3$-phenyl | 4-CH$_3$-phenyl-SO$_2$- | CH$_3$ | M.p.: 180–190° C. |
| IV-6 | 4-CH$_3$-phenyl | H | CH$_3$ | M.p.: 206–207° C. |

$^{a)}$$^1$H-NMR (DMSO, δ, ppm) for R$^3$ = CH$_3$

STARTING SUBSTANCES OF THE FORMULA (XI)

Example (XI-1)

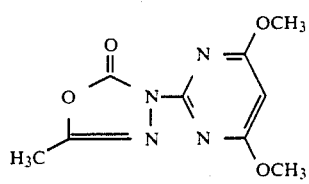

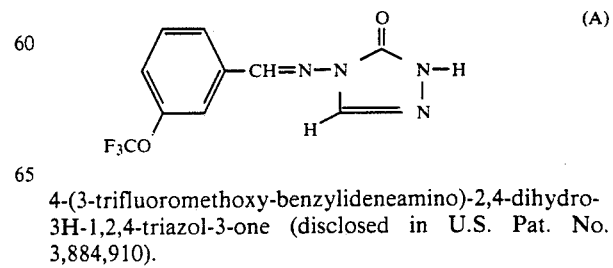

4-(3-trifluoromethoxy-benzylideneamino)-2,4-dihydro-3H-1,2,4-triazol-3-one (disclosed in U.S. Pat. No. 3,884,910).

Example A

POST-EMERGENCE TEST

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is chosen such that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, for example, the compounds according to Preparation Examples: (1), (2), (3), (4), (92), (208) and (210) show a clearly superior activity compared with the prior art.

Example B

PRE-EMEGENCE TEST

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is scored in % damage in comparison to the development of the untreated control. The figures denote:

0% = no action (like untreated control)
100% = total destruction

In this test, for example the compounds of Preparation Examples: (1), (2), (3), (4), (208) and (210) have a clearly superior activity compared with the prior art.

It will be appreciated that the instant specification and claims are set forth by way of illustration and not limitation, and that various modifications and changes may be made without departing from the spirit and scope of the present invention.

What is claimed is:

1. A compound of the formula

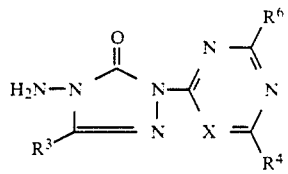

in which
   $R^3$ represents hydrogen, fluorine, chlorine, bromine, iodine, hydroxyl, mercapto, amino or an optionally fluorine- and/or chlorine-substituted radical selected from the group consisting of $C_1$-$C_4$-alkyl, $C_3$-$C_6$-cycloalkyl, benzyl, phenyl, $C_1$-$C_4$-alkoxy, $C_3$-$C_4$-alkenyloxy, $C_3$-$C_4$-alkinyloxy, $C_1$-$C_4$-alkylthio, $C_1$-$C_4$-alkylsulphinyl, $C_1$-$C_4$-alkylsulphonyl, $C_3$-$C_4$-alkenylthio, $C_3$-$C_4$-alkinylthio, benzyloxy, benzylthio, $C_1$-$C_4$-alkylamino and di-($C_1$-$C_4$-alkyl)-amino,
   $R^4$ represents hydrogen, fluorine, chlorine, bromine, hydroxyl, amino, $C_1$-$C_4$-alkyl, $C_1$-$C_4$-halogenoalkyl, $C_1$-$C_2$-alkoxy-$C_1$-$C_2$-alkyl, $C_1$-$C_4$-alkoxy, $C_1$-$C_4$-halogenoalkoxy, $C_1$-$C_2$-alkoxy-$C_1$-$C_2$-alkoxy, $C_1$-$C_4$-alkylthio, $C_1$-$C_4$-halogenoalkylthio, $C_1$-$C_4$-alkylsulphinyl, $C_1$-$C_4$-alkylsulphonyl, $C_1$-$C_4$-alkylamino or di-($C_1$-$C_2$-alkyl)-amino, and
   $R^6$ represents hydrogen, fluorine, chlorine, bromine, $C_1$-$C_4$-alkyl, $C_1$-$C_4$-alkoxy, $C_1$-$C_4$-halogenoalkoxy, $C_1$-$C_4$-alkylthio, $C_1$-$C_4$-alkylsulphinyl, $C_1$-$C_4$-alkylsulphonyl, $C_1$-$C_4$-alkylamino, dimethylamino or diethylamino,
or a salt thereof.

2. A compound or salt according to claim 1, in which
   $R^3$ represents hydrogen, methyl, ethyl, propyl, isopropyl, trifluoromethyl, cyclopropyl, benzyl, phenyl, t-butyl, s-butyl, i-butyl, n-butyl, methoxy or methylthio,
   $R^4$ represents hydrogen, fluorine, chlorine, bromine, methyl, trifluoromethyl, methoxy, ethoxy, difluoromethoxy, methylthio, ethylthio, amino, methylamino, ethylamino, dimethylamino or diethylamino, and
   $R^6$ represents hydrogen, fluorine, chlorine, bromine, methyl, ethyl, methoxy, ethoxy, propoxy, isopropoxy, difluoromethoxy, methylthio, ethylthio, methylamino, ethylamino, dimethylamino or diethylamino.

3. A compound according to claim 1, wherein such compound is 4-amino-5-methyl-2-(4,6-dimethoxy-1,3,5-triazin-2-yl)-2,4-dihydro-3H-1,2,4-triazol-3-one of the formula

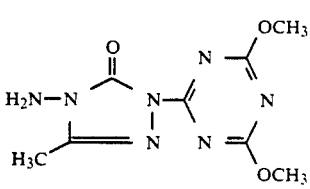

or a salt thereof.

4. A compound according to claim 1, wherein such compound is 4-amino-5-methylthio-2-(4,6-dimethoxy-1,3,5-triazin-2-yl)-2,4-dihydro-3H-1,2,4-triazol-3-one of the formula

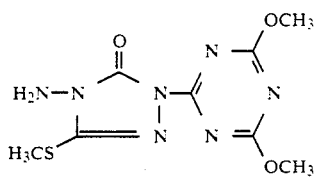
or a salt thereof.
5. A compound according to claim 1, wherein such compound is 4-amino-5-isopropyl-2-(4,6-dimethoxy-1,3,5-triazin-2-yl)-2,4-dihydro-3H-1,2,4-triazol-3-one of the formula
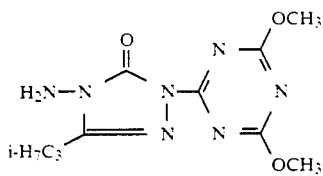
or a salt thereof.
6. A compound according to claim 1, wherein such compound is 4-amino-2-(4,6-dimethoxy-1,3,5-triazin-2-yl)-2,4-dihydro-3H-1,2,4-triazol-3-one of the formula
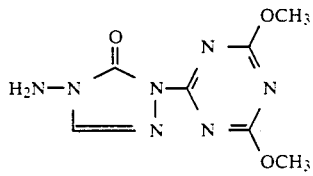
or a salt thereof.
* * * * *

UNITED STATES PATENT AND TRADEMARK OFFICE
CERTIFICATE OF CORRECTION

PATENT NO. : 5,151,514
DATED : September 29, 1992
INVENTOR(S) : Muller et al.

It is certified that error appears in the above-identified patent and that said Letters Patent is hereby corrected as shown below:

Col. 76, line 5  Delete " 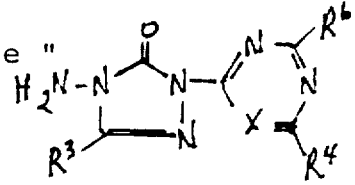 " and substitute

-- 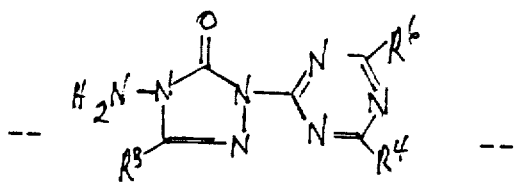 --

Signed and Sealed this

Nineteenth Day of July, 1994

Attest:

BRUCE LEHMAN

Attesting Officer   Commissioner of Patents and Trademarks